US011353155B2

(12) United States Patent
Bouchard

(10) Patent No.: US 11,353,155 B2
(45) Date of Patent: Jun. 7, 2022

(54) COUPLING SYSTEMS

(71) Applicant: TECHNOLOGIES CGC INC., Quebec (CA)

(72) Inventor: Carl Bouchard, Quebec (CA)

(73) Assignee: TECHNOLOGIES CGC INC., Quebec (CA)

( * ) Notice: Subject to any disclaimer, the term of this patent is extended or adjusted under 35 U.S.C. 154(b) by 0 days.

(21) Appl. No.: 17/503,672

(22) Filed: Oct. 18, 2021

(65) Prior Publication Data

US 2022/0034444 A1 Feb. 3, 2022

Related U.S. Application Data

(63) Continuation of application No. PCT/CA2020/051329, filed on Oct. 2, 2020.

(60) Provisional application No. 62/909,408, filed on Oct. 2, 2019.

(51) Int. Cl.
*F16M 11/00* (2006.01)
*F16M 11/04* (2006.01)
*F16M 13/02* (2006.01)

(52) U.S. Cl.
CPC ........ *F16M 11/041* (2013.01); *F16M 13/022* (2013.01); *F16M 2200/028* (2013.01)

(58) Field of Classification Search
CPC .............. F16M 11/041; F16M 13/022; F16M 2200/028
USPC ................................ 248/637, 279.1; 403/345
See application file for complete search history.

(56) References Cited

U.S. PATENT DOCUMENTS

| 4,511,158 | A | 4/1985 | Varga et al. |
| 5,152,486 | A | 10/1992 | Kabanek et al. |
| 5,362,021 | A | 11/1994 | Phillips |
| 9,746,125 | B2 * | 8/2017 | Bowman .............. F16M 11/041 |
| 11,007,951 | B1 * | 5/2021 | Zarecky .................... B62B 5/00 |
| 2002/0011543 | A1 | 1/2002 | Chinn et al. |
| 2003/0046764 | A1 | 3/2003 | Smeed |

(Continued)

FOREIGN PATENT DOCUMENTS

DE 102017110001 A1 11/2018

OTHER PUBLICATIONS

International Search Report of PCT/CA2020/051329; Search completed on Nov. 25, 2020.

(Continued)

*Primary Examiner* — Todd M Epps
(74) *Attorney, Agent, or Firm* — BCF LLP

(57) ABSTRACT

A coupling device comprising a base member connectable to a first item and a release member connectable to a second item, the base and release members being releasably connectable together. The base member has a front face including a pocket. The release member comprises a body which is configured to be received in the pocket in a coupled position. The pocket has an open access end through which the release member can be slidingly inserted and removed. The base member includes a stop member moveable, by an actuator, between a lock position in which the stop member interengages with the release member to prevent removal of the release member from the pocket of the base member, and a release position in which the release member can be separated from the base member. A securing apparatus for releasably securing a mobile equipment to a support surface, and including the coupling device.

23 Claims, 14 Drawing Sheets

(56) References Cited

U.S. PATENT DOCUMENTS

| | | |
|---|---|---|
| 2008/0217910 A1 | 9/2008 | Walke |
| 2012/0262039 A1 | 10/2012 | Daugbjerg et al. |
| 2014/0374564 A1 | 12/2014 | Schroeder et al. |
| 2014/0374565 A1* | 12/2014 | Tan .................. F16F 15/03 248/542 |
| 2015/0041419 A1 | 2/2015 | Hasegawa |
| 2015/0090849 A1 | 4/2015 | Breitweiser et al. |
| 2015/0273138 A1 | 10/2015 | Wolff et al. |
| 2016/0031382 A1 | 2/2016 | Chinn et al. |
| 2016/0324701 A1 | 11/2016 | Cambridge et al. |
| 2017/0209318 A1 | 7/2017 | Schroeder et al. |

OTHER PUBLICATIONS

International Search Report of PCT/CA2020/051392; Search completed on Dec. 7, 2020.
International Search Report of PCT/CA2020/050253; Search completed on May 19, 2021.
International Search Report of PCT/CA2020/050685; Search completed on Aug. 25, 2021.
International Search Report of PCT/CA2021/050706; Search completed on Jul. 9, 2021.

* cited by examiner

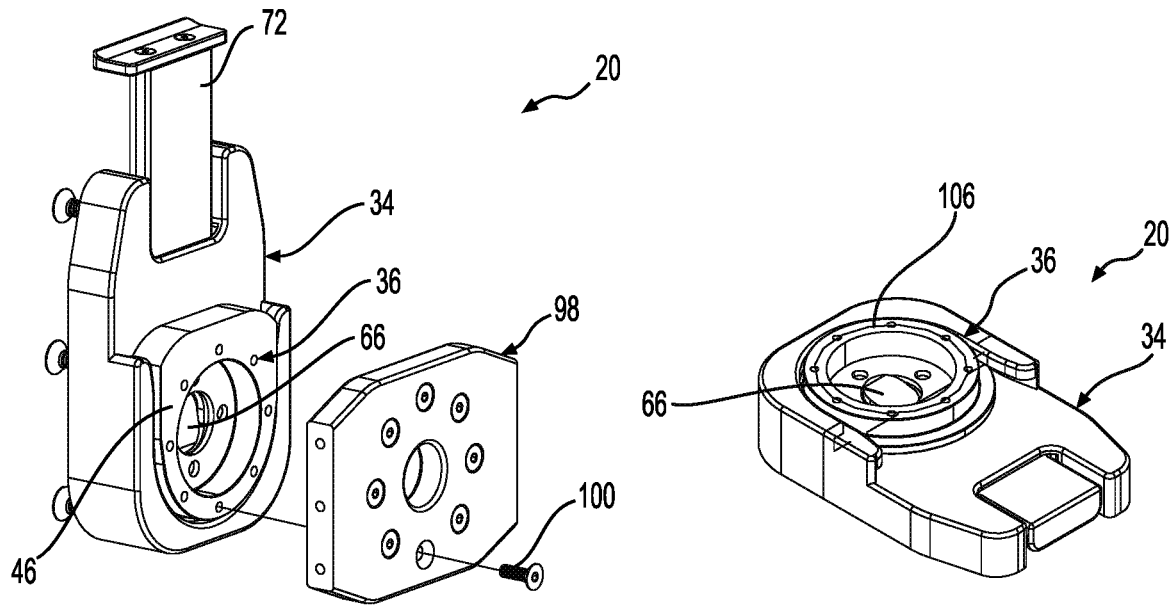
FIG. 16
FIG. 17
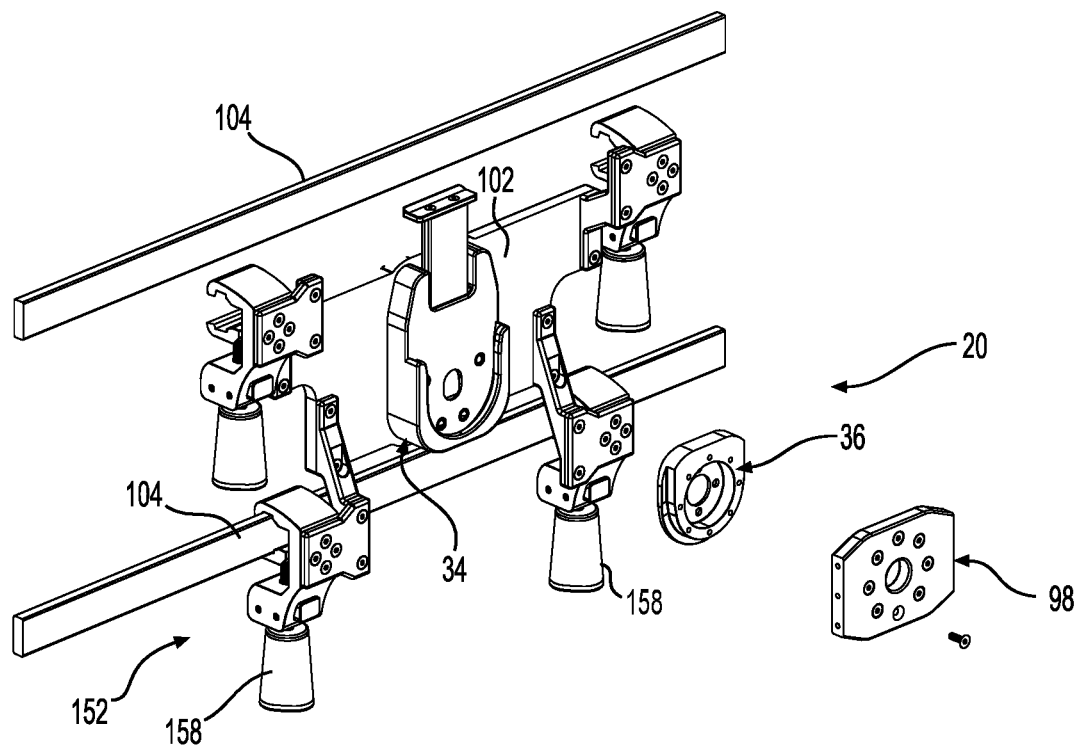
FIG. 18

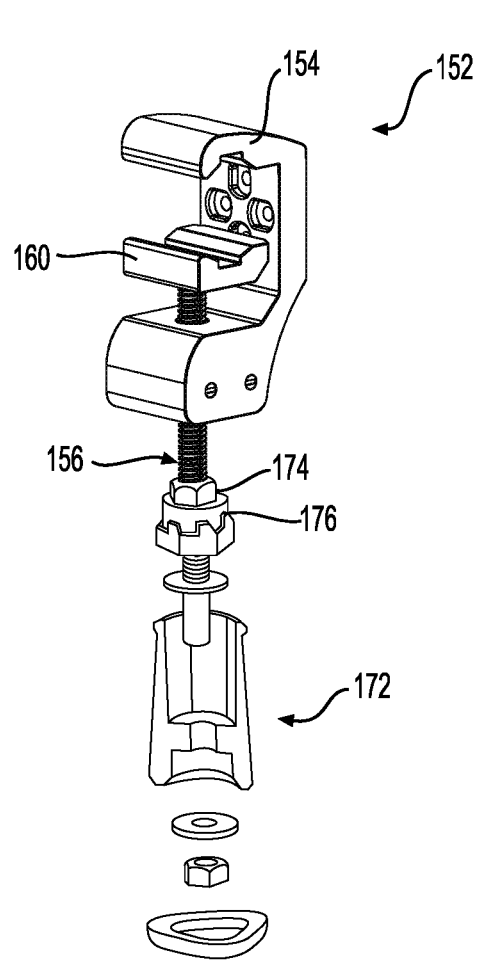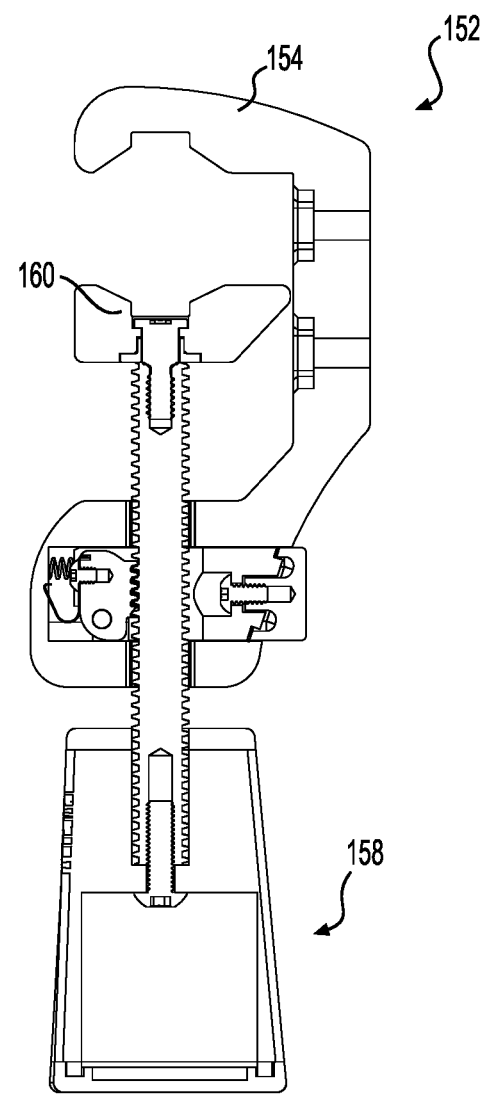
FIG. 23  FIG. 24

COUPLING SYSTEMS

FIELD OF THE DISCLOSURE

The present disclosure relates to coupling systems for releasably securing mobile equipment to a support surface.

BACKGROUND OF THE DISCLOSURE

In the transportation of mobile equipment, various systems exist for securing the mobile equipment to a support surface of a transport vehicle.

In the case of mobile equipment which comprises medical equipment relating to a patient, there are particular considerations. When transporting a patient there is usually medical equipment that accompanies the patient and the transportation personnel. In the case of land or air ambulances, the ambulance personnel are responsible for following and securing the medical equipment. Regulations, according to states and provinces, require the medical equipment to be secured during transportation to prevent injuries as well as damage to the equipment.

Current solutions for securing medical equipment during transportation include attaching the medical equipment near the patient with straps or seat belts. The medical equipment is also sometimes placed on the patients themselves.

However, these current solutions are not ideal. They do not secure the medical equipment in a manner which allows for secure restraint as well as quick and easy release. They also do not take into account the vibrations and forces that the medical equipment may experience depending on the transportation vehicle, and the road/air conditions.

Furthermore, certain existing solutions are not able to be used with different medical devices from a multitude of companies, and tend to be specialized to a particular equipment.

These issues are confounded by the requirement that certain medical equipment have components that must be prominently displayed during transportation and/or accessible by transportation personnel. Further, certain mobile equipment is not designed for transportation and therefore do not have handles or devices to secure them.

Therefore, there is a need for coupling systems which overcome or reduce at least some of the above-described problems.

SUMMARY OF THE DISCLOSURE

Broadly, from one aspect, there is provided a coupling device for releasably securing a first item to a second item, the coupling device comprising a base member connectable to the first item, and a release member connectable to the second item, the base member and the release member being releasably connectable together in a lockable coupled position; the release member comprising a body which is configured to be received in a pocket on a front face of the base member, the pocket having an open access end through which the release member can be slidingly inserted in a coupled position; the base member including a stop member moveable, by an actuator, between a lock position in which the stop member interengages with the release member to prevent removal of the release member from the pocket of the base member in the coupled position, and a release position in which the release member can be separated from the base member. The front face of the base member may include a contact portion for contacting a contact face of the release member. The first item may be a portion of a support surface such as a wall, floor or ceiling, or a portion of patient transportation such as a stretcher, wheelchair or a bed. The second item may be a portion of equipment, such as medical equipment.

In certain embodiments, the base member has a shoulder extending around the contact portion to define the pocket for receiving the release member, the shoulder engageable with a portion of a flange of the release member when the release member is positioned on the base member.

In certain embodiments, the stop member is positioned in a recess within the contact portion of the base member and moveable, by the actuator which is connected to a resilient lock mechanism, between the lock position in which at least a portion of the stop member extends from the recess and abuts an edge of an opening defined in the release member contact face in the coupled position, and a release position in which the stop member is retracted into the recess.

In certain embodiments, the stop member has a wedge shaped portion with a thinner end of the wedge facing the open access end of the pocket, and wherein the resilient lock mechanism is configured to permit the stop member to move into the recess as the release member is slid into the pocket.

In certain embodiments, the actuator has a neutral position and a deployed position, wherein when the actuator is in the neutral position, the stop member is resiliently biased towards the lock position.

In certain embodiments, the base member comprises a plurality of spring loaded ball bearings partially extending from recesses formed in the front face of the base member and engageable with corresponding recesses defined in the contact face of the release member.

In certain embodiments, the contact face of the release member has an anti-friction layer.

In certain embodiments, the coupling device further comprises a damping member attachable to a back face of the base member and arranged to be positioned between the base member and the first item in use, the damping member being arranged to absorb vibration and/or shock.

In certain embodiments, the coupling device further comprises a top plate attachable to the collar of the release member and attachable to the second item.

In certain embodiments, a perimeter of the body of the release member is circular in shape, such that the release member can be rotated within the pocket in one or both of the lock position and the release position when the base member is coupled to the release member.

In certain embodiments, the stop member functions as a rotation point and is positioned substantially centrally of the contact portion of the base member.

In certain embodiments, a perimeter of the body of the release member has an eccentric shape such that the release member is not rotatable in the pocket of the base member when the base member is coupled to the release member.

In certain embodiments, the shoulder is configured to delimit movement of the release member orthogonally away from the front face of the base member, when the base member and the release member are in the coupled position.

From another aspect, there is provided a coupling device for releasably securing a mobile equipment to a support surface, the coupling device comprising a base member connectable to the support surface, and a release member connectable to the mobile equipment, the base member and the release member being releasably connectable together in a coupled position; the release member comprising a plate-like body with a first side, the first side defining a planar contact face, and a second side having a collar extending therefrom, the collar positioned inwardly of a perimeter of the release member to define a flange portion; the base member having: a front face including a planar contact portion for contacting the contact face of the release member; a shoulder extending around a portion of a periphery of the planar portion to define a pocket for receiving the release member, the shoulder engageable with a portion of the flange of the release member when the release member is positioned on the base member; an open access end through which the release member can be slidingly inserted and removed from the pocket; a stop member positioned in a recess within the planar contact portion and moveable by a resilient lock mechanism and an actuator between a lock position in which at least a portion of the stop member extends from the recess and abuts an edge of an opening defined in the release member contact face in the coupled position, and a release position in which the stop member is retracted into the recess; the actuator having a neutral position and a deployed position, wherein when the actuator is in the neutral position, the stop member is resiliently biased towards the lock position.

In certain embodiments, the base member comprises a plurality of spring loaded ball bearings partially extending from recesses formed in the front face of the base member and engageable with corresponding recesses defined in the planar contact face of the release member.

In certain embodiments, the planar contact face of the release member has an anti-friction layer.

In certain embodiments, the coupling device further comprises a damping member attachable to a back face of the base member and arranged to be positioned between the base portion and the surface in use, the damping member being arranged to absorb vibration and/or shock.

In certain embodiments, the coupling device further comprises a top plate attachable to the collar of the release member and attachable to the mobile equipment.

In certain embodiments, the perimeter of the plate-like body of the release member is circular in shape, the stop member of the base member is positioned substantially centrally of the planar contact portion, and the opening of the release member is positioned substantially centrally of the plate-like body, such that the release member can be rotated within the pocket when the stop member is in the lock position.

In certain embodiments, the perimeter of the plate-like body of the release member has an eccentric shape such that the release member is not rotatable in the pocket of the base member.

From another aspect, there is provided a securing apparatus for releasably securing a mobile equipment to a support surface, the apparatus comprising at least one support member attachable to the mobile equipment. Optionally, the securing apparatus includes a coupling device, as defined herein, attachable to the at least one support member of the securing apparatus.

In certain embodiments, support member is a base support member for supporting a base of the mobile equipment.

In certain embodiments, the base support member comprises a plate having raised portions along at least a portion of a perimeter of the plate.

In certain embodiments, the support member comprises a backing support member for supporting a back of the mobile equipment, wherein the backing support member comprises a pair of struts extending upwardly from the base support member.

In certain embodiments, the backing support member includes a coupling device, as described herein, attached thereto for releasably attaching the mobile equipment.

In certain embodiments, the support member further comprises a top restraining member for engaging a top face of the mobile equipment and extending across a top of the mobile equipment in use, the top restraining member comprising two arms, each arm having a proximal end pivotally attached to a top end of the backing support member, the arms being pivotable between a restraining position in which they extend across the top of the mobile equipment, and a release position in which they extend upwardly from the backing support member; further comprising a locking mechanism for locking the arms in one or both of the restraining position and the release position.

In certain embodiments, each arm has a distal end having a claw extending along a portion of a front face of the mobile equipment.

In certain embodiments, the locking mechanism comprises a spring and a pin and an unlocking bar at the proximal end of the elongate members, wherein pulling on the unlocking bar causes the locking mechanism to unlock and permit movement between the two positions.

In certain embodiments, the securing apparatus further comprises at least one clamp attached to the support member for releasably attaching the support member to the support surface.

In certain embodiments, the clamp comprises a main body, a clamping screw, a handle, a movable jaw and a disengagement mechanism to release the clamping screw, the disengagement mechanism comprising a slider moveable by a button and in engagement with the clamping screw; and a cam having a thread engageable with a thread of the clamping screw and pivotable relative to the clamping screw to engage and disengage the threads of the clamping screw by modulation of the button.

In certain embodiments, the handle is a torque handle.

In certain embodiments, the securing apparatus further comprises at least one hook attached to the support member for releasably attaching the support member to the support surface.

In certain embodiments, the at least one hook has a free end and a pivot end to which it is attached to the support member, and is moveable by the pivot end between a deployed position in which the free end extends away from the support plate, and a retracted position in which the at least one hook lies against the support member or another hook.

In certain embodiments, there are at least two hooks, spaced from one another, the at least two hooks being resiliently biased to the retracted position in which they are arranged to overlap one another.

In certain embodiments, the securing apparatus further comprises an IV pole mounting member, for mounting an IV pole in a substantially vertical position.

In certain embodiments, the securing apparatus further comprises an IV pole locking mechanism comprising a locking plate having a rod lock slot, through which an end of the IV pole is extended, and a spring resiliently biasing the plate away from the securing apparatus.

In certain embodiments, the securing apparatus further comprises an IV pole retaining member attached to the support member and arranged to receive and secure an IV pole in a horizontal storage position whilst not in use.

From another aspect, there is provided a securing apparatus for releasably securing a mobile equipment to a support surface, the securing apparatus comprising:—three support members for supporting a mobile equipment, the three support members comprising:—a base support member for supporting a base of the mobile equipment, —a backing support member for supporting a back of the mobile equipment, and—a top restraining member for engaging a top face of the mobile equipment and extending across a top of the mobile equipment in use; and—a coupling device comprising a base member connectable to the support surface, and a release member connectable to one of the support members, the base member and the release member being releasably connectable together in a coupled position. In certain embodiments, the coupling device is as defined herein.

Advantages

In certain embodiments, the mobile equipment is fragile apparatus and/or medical equipment. The support surface may comprise one or more of a wall, a ceiling or a floor of a transport vehicle. The support surface may also comprise rails or poles within the transport vehicle, or items related to support of the patient such as a stretcher or a wheelchair. The support vehicle may be a car, an ambulance, a helicopter, an airplane, a boat, a submarine, a space vehicle, and the like. In this way, the mobile equipment may be securable close to the patient and the transportation personnel.

Embodiments of one or more of the securing apparatus, clamp and coupling device enable the securing of the mobile equipment to the support surface during transportation or other multi-directional movement. Transportation could be off-road and jarring. The mobile equipment can remain secured to the support surface during high acceleration and deceleration events, as well as travel on uneven surfaces. In certain embodiments, the securing apparatus can withstand impacts of up to 30G.

Embodiments of one or more of the securing apparatus, clamp and coupling device enable the securing and the release of the mobile equipment by a single person, and do not require more than one person.

Embodiments of one or more of the securing apparatus, clamp and coupling device enable the unconstrained use of the mobile equipment during transportation by allowing access to required parts of the mobile equipment, and not obscuring or blocking those parts.

Embodiments of one or more of the securing apparatus, clamp and coupling device enable the securing of mobile equipment of different sizes, shapes and configurations to support surfaces.

Embodiments of one or more of the securing apparatus, clamp and coupling device enable the mobile equipment to be easily secured and removed to the support surface by a sliding action to couple the base member and the release member of the coupling device. Release of the mobile equipment from the support surface can be achieved by a single push button. Rotation of the mobile equipment whilst the mobile equipment is retained on the support surface is possible in certain embodiments of the coupling device that permit rotation.

Definitions

It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

As used herein, the term "and/or" is to be taken as specific disclosure of each of the two specified features or components with or without the other. For example "A and/or B" is to be taken as specific disclosure of each of (i) A, (ii) B and (iii) A and B, just as if each is set out individually herein.

BRIEF DESCRIPTION OF DRAWINGS

Further aspects and advantages of the present invention will become better understood with reference to the description in association with the following in which:

FIG. 16 is a coupling device comprising a base member, a release member, and a top plate, according to certain other embodiments of the present disclosure.

FIG. 17 is the coupling device of FIG. 16, with the top plate removed for clarity, and including a circular member, according to certain embodiments of the present disclosure.

FIG. 18 is an exploded view of the coupling device of FIG. 16 mounted to rails, according to certain embodiments of the present disclosure.

FIG. 23 is a clamp for use with the securing apparatus of FIG. 1, according to certain other embodiments of the present disclosure.

FIG. 24 is a cross-sectional view of the clamp of FIG. 22, according to certain other embodiments of the present disclosure.

DETAILED DESCRIPTION

Figure 1:
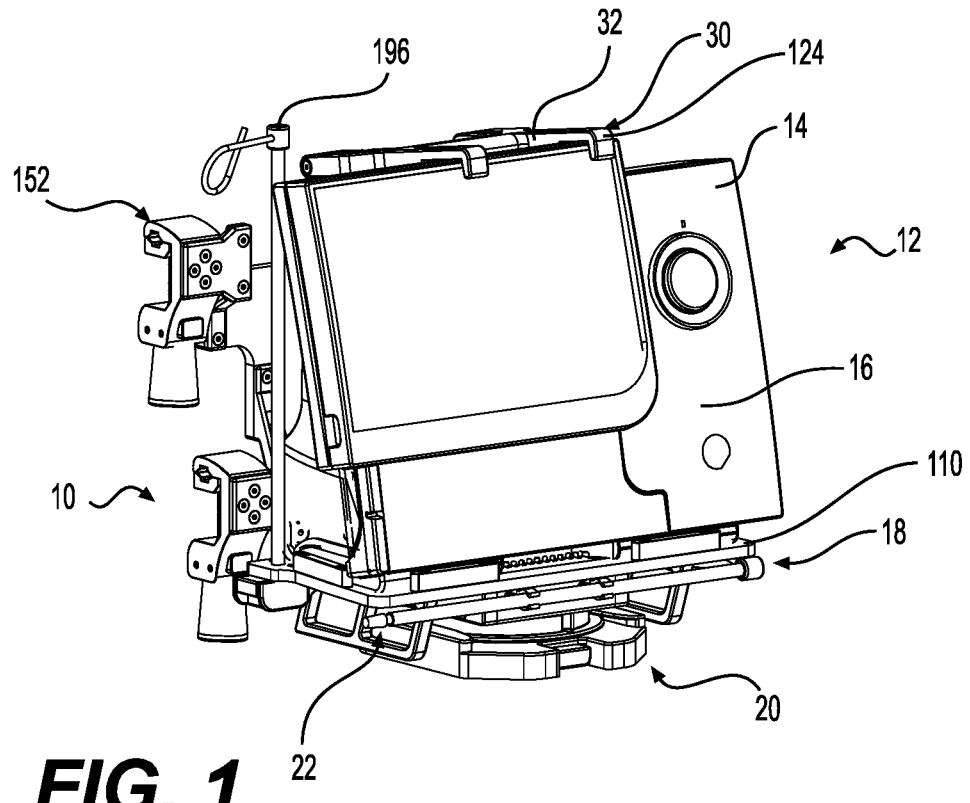
FIG. 1 is a perspective view from the front of a securing apparatus comprising a coupling device and a clamp, according to certain embodiments of the present disclosure.
Figure 2:
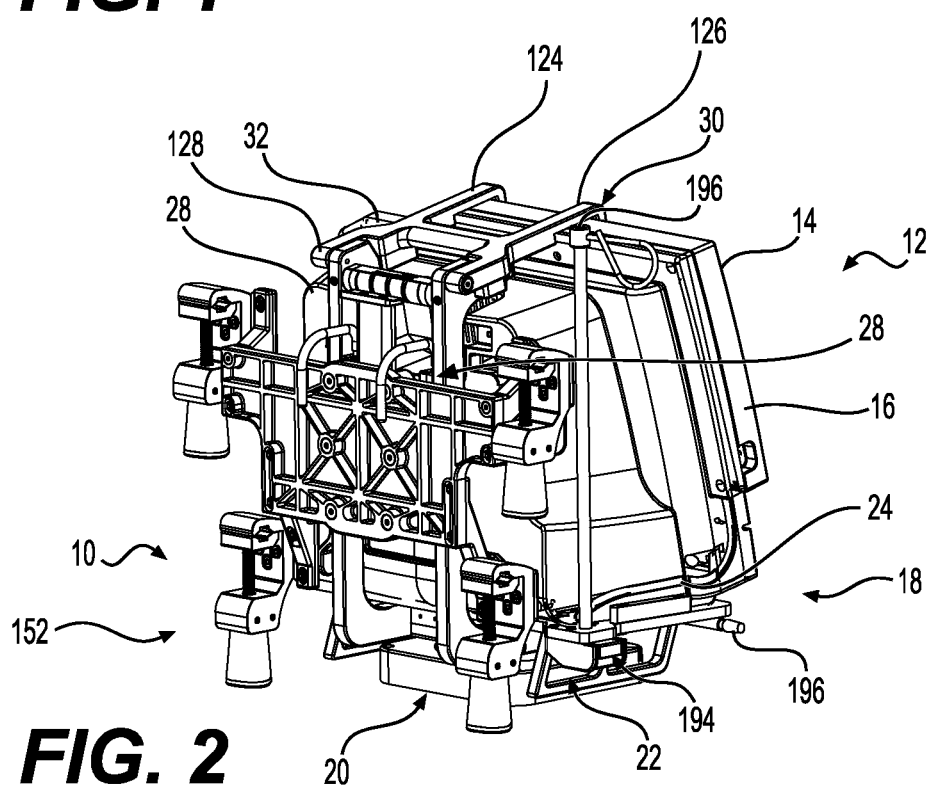
FIG. 2 is a perspective view from the back of the securing apparatus of FIG. 1, according to certain embodiments of the present disclosure.
Figure 3:
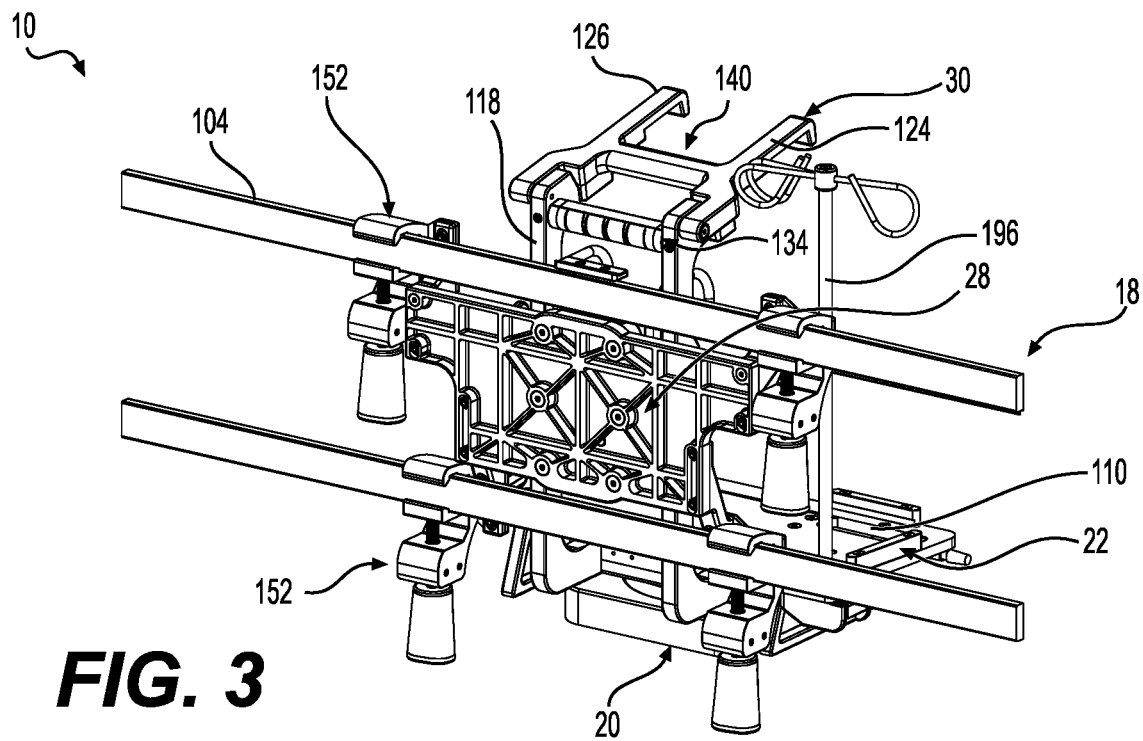
FIG. 3 is a perspective view from the back of the securing apparatus of FIG. 1 when attached to rails, according to certain embodiments of the present disclosure.
Figure 4:
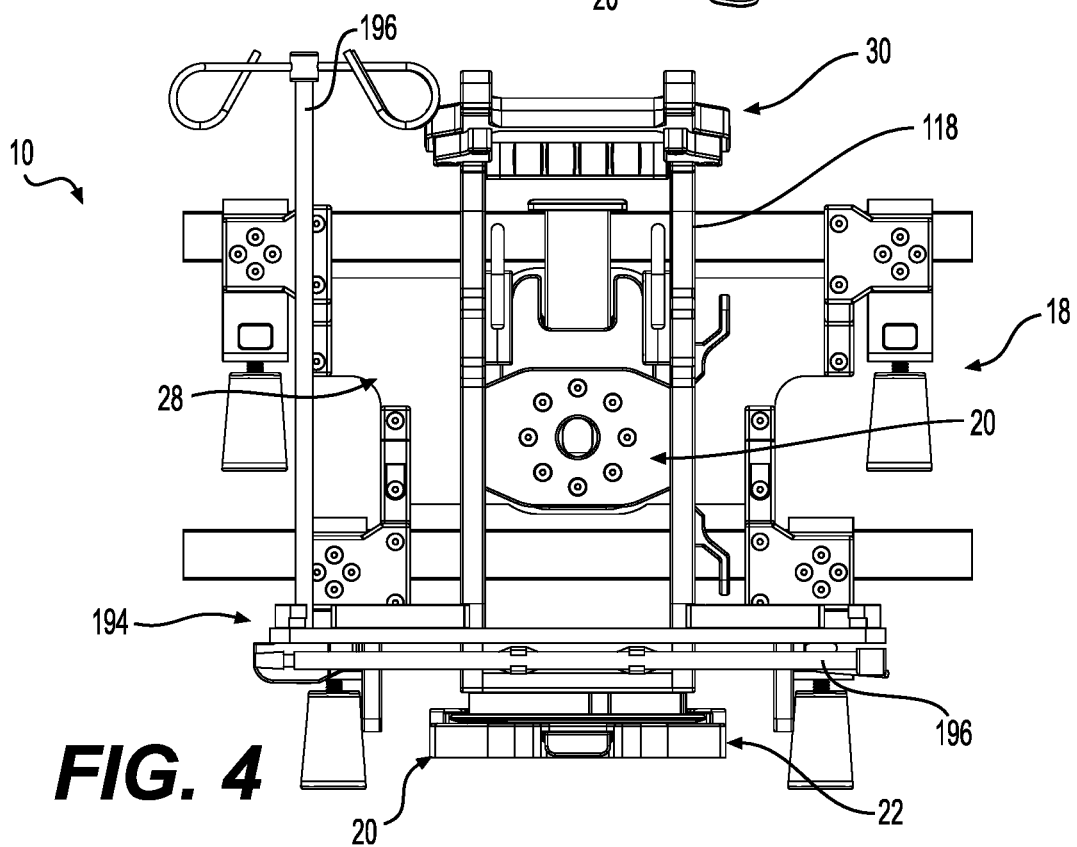
FIG. 4 is a front plan view of the securing apparatus of FIG. 1 when attached to rail, according to certain embodiments of the present disclosure.
Figure 5:
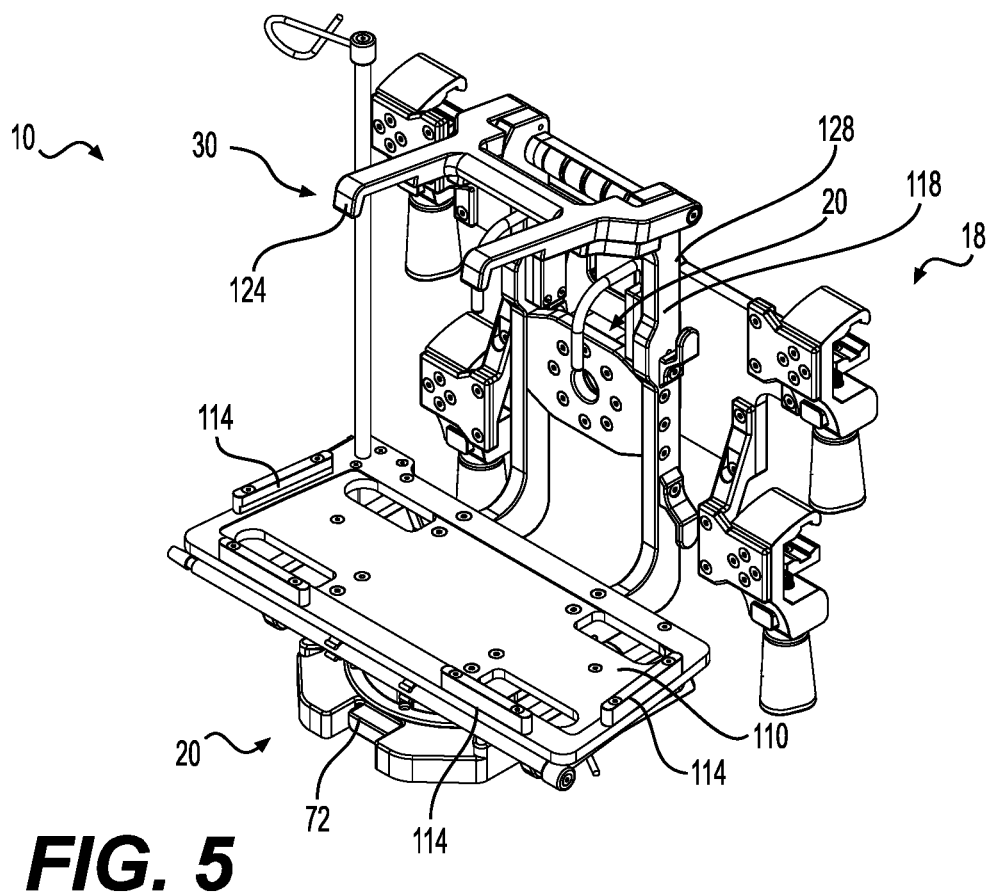
FIG. 5 is a perspective view from the front of a securing apparatus comprising a coupling device, according to certain other embodiments of the present disclosure.

The present disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items. In the following description, the same numerical references refer to similar elements.

Broadly, there is provided a securing apparatus 10 for releasably securing a mobile equipment 12 to a support surface or to a coupling device 20. In certain embodiments which will be described below, the mobile equipment 12 is medical equipment and the support surface is a wall, ceiling or floor of a vehicle. The vehicle can be any landborne or airborne vehicle such as an ambulance, a helicopter or an airplane. The mobile equipment 12 can be any type of equipment that accompanies a patient during transit in the vehicle, such as ventilators, pumps, monitoring equipment, drips, etc. In certain embodiments, the securing apparatus 10 for such mobile equipment 12 is arranged to secure and release the mobile equipment 12 in one or both of a quick release manner. Preferably one of the release or securing operations can be performed single-handedly by an operator of the securing apparatus 10.

Referring initially to FIGS. 1 to 6, there are shown certain embodiments of the securing apparatus 10 holding a mobile equipment 12, which is a monitoring device 14 having a screen 16. The securing apparatus 10 comprises a frame 18 for supporting the mobile equipment, the frame 18 having one or more support members, and the coupling device 20 associated with the frame 18 and releasably attachable to the mobile equipment 12. One or more of the support members are attachable to the support surface. The coupling device 20 will be described in further detail below.

In the embodiments illustrated in FIGS. 1 to 6, the frame 18 comprises a plurality of support members for supporting the mobile equipment 12 whilst allowing access to the mobile equipment: a base support member 22 for supporting a bottom face 24 of the mobile equipment 12, a backing support member 26 for supporting a back face 28 of the mobile equipment 12, and a top restraining member 30 for engaging a top and/or front face 32 of the mobile equipment 12. As illustrated in FIGS. 1 to 6, coupling devices 20 are attached to both the base support member 22 and the backing support member 26. However, in other embodiments, the coupling device 20 may be provided in association with at least one of the base support member 22, the backing support member 26, and the top restraining member 30.

In certain embodiments, the securing apparatus 10 may be provided without the coupling device 20. In certain embodiments, the securing apparatus 10 may be provided with only some of the support elements.

Turning now to the coupling device 20 shown in FIGS. 7 to 14. It will be appreciated that the coupling device 20 may be used to releasably connect any two items or elements together, such as a first item and a second item. The first and second items may comprise one or more of a support surface, a transportation device such as a wheelchair, a stretcher or a bed, equipment such as medical equipment, securing apparatus for equipment such as the securing apparatus 10. The coupling device 20 herein presented below and in the drawings is described in relation to the securing apparatus 10 but its use is not limited to such.

The coupling device 20 comprises a base member 34 connectable to the support surface, and a release member connectable to the mobile equipment 12, the base member 34 and the release member 36 being releasably connectable together in a coupled position.

The release member 36 has a body 38 which is a plate-like and has a first side 40 and a second side 42. The first side 40 of the release member body 38 defines a planar contact face 44 for contacting the base member 34. The second side 42 of the release member 36 has a collar 46 extending therefrom, the collar 46 positioned inwardly of a perimeter 48 of the release member 36 to define a flange portion 50 of the release member 36.

The base member 34 has a front side 52 and a back side 54. The front side 52 has a planar contact portion 56 for contacting the contact face 44 of the release member 36. A shoulder 58 extends around a portion of a periphery 60 of the planar contact portion 56 to define a pocket 62 for receiving at least a portion of the release member 36. The shoulder 58 is engageable with a portion of the flange 50 of the release member 36 when the release member 36 is positioned on the base member 34.

The base member front side 52 has an open access end 64 through which the release member 36 can be slidingly inserted and removed from the pocket 62. As can be seen, the base member 34 is four-sided, with the shoulder 58 extending around three of the four sides and the fourth side being the open access end 64. In other embodiments, the base member 34 may have different numbers of sides.

Figure 7:
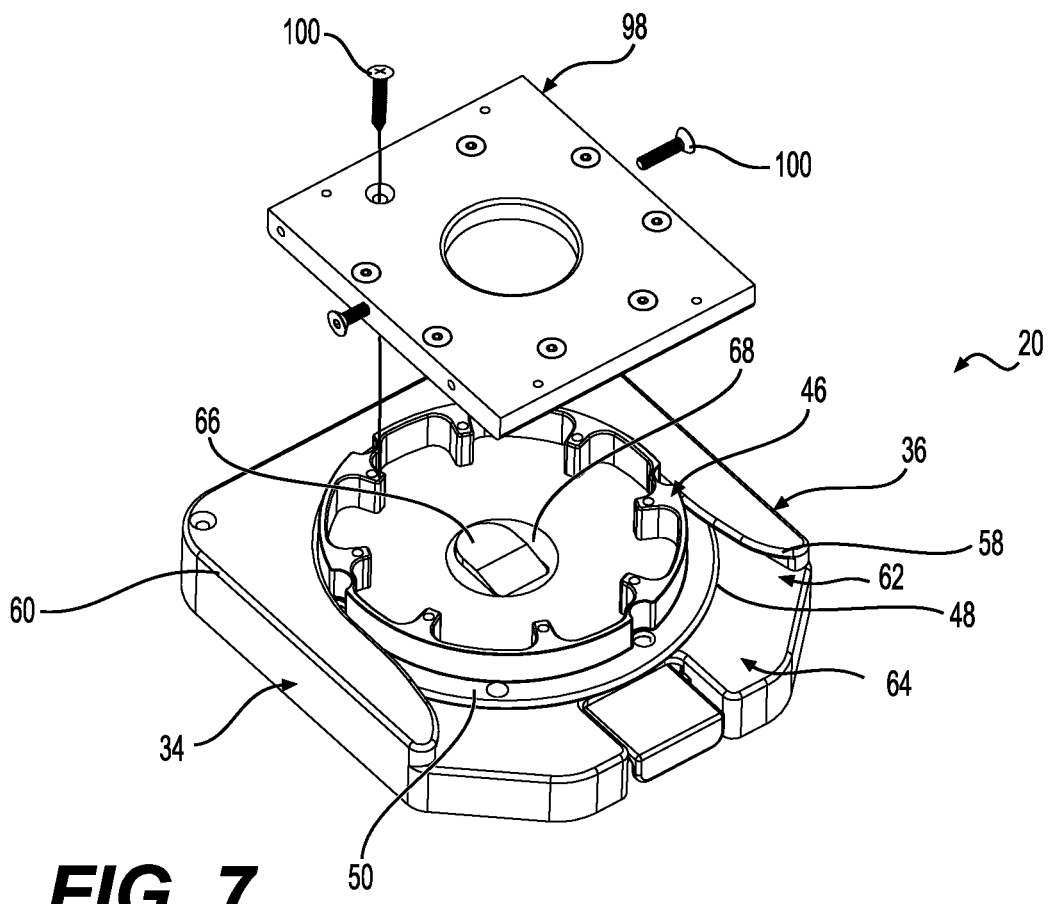
FIG. 7 is a coupling device comprising a base member, a release member, and a top plate, according to certain embodiments of the present disclosure.
Figure 8:
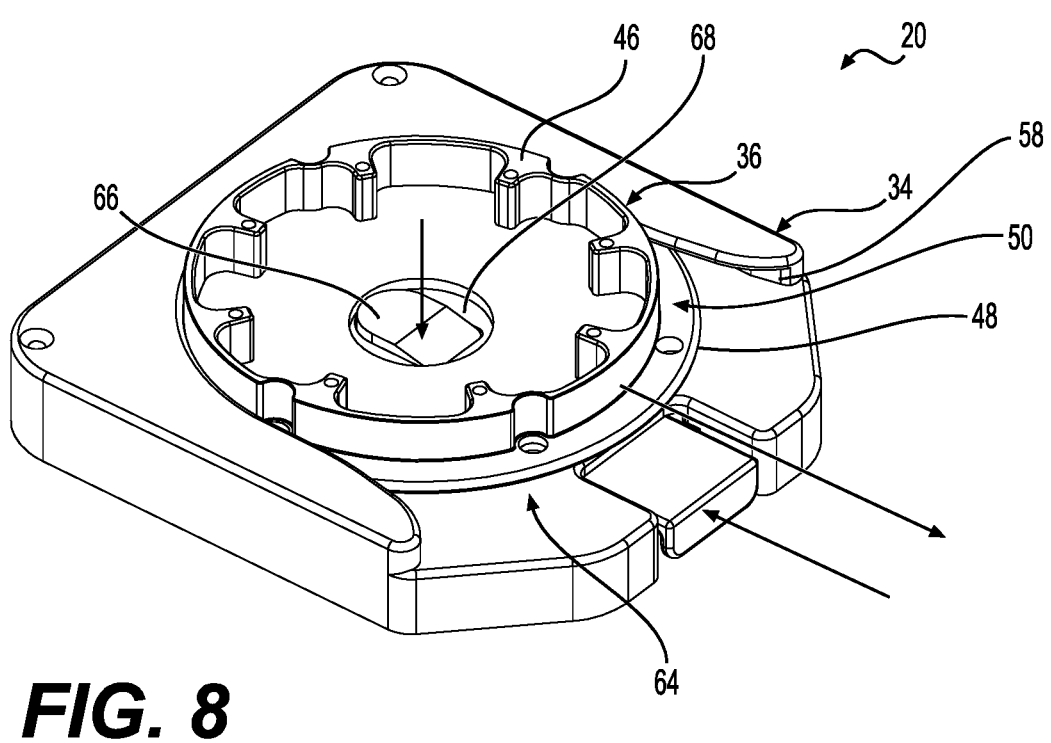
FIG. 8 is the coupling device of FIG. 7, with the top plate removed for clarity, when in the coupled and lock position, according to certain other embodiments of the present disclosure.
Figure 9:
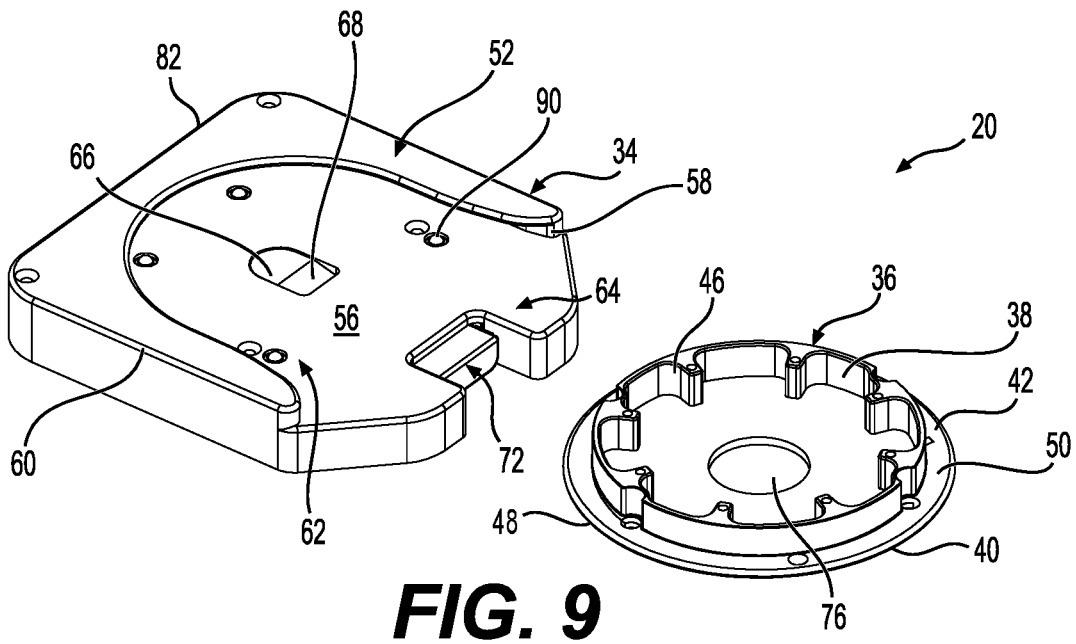
FIG. 9 is the coupling device of FIG. 8, when in the uncoupled and unlock position, according to certain other embodiments of the present disclosure.

A stop member 66 is positioned in a recess 68 within the planar contact portion 56 of the base member 34 and is moveable relative to the planar contact portion 56. The stop member 66 is moveable to extend out of the recess 68 and to be housed fully in the recess 68 by a coupling lock mechanism 70 and an actuator 72. The stop member 66 is actuatable between a lock position in which at least a portion of the stop member 66 extends from the recess 68 and a release position in which the stop member 66 is retracted into the recess 68 and does not extend from the recess 68. In the lock position, when the base member 34 and the release member 36 are coupled together, the stop member 66 can abut an edge 74 of an opening 76 defined in the release member contact face 44 to delimit movement of the release member 36 towards the open access end 64 (FIGS. 7 and 8). In the release position, the release member 36 can be decoupled from the base member 34 (FIG. 9).

The actuator 72 is positioned at the open access end 64. In the embodiments illustrated in FIGS. 7 to 13, the actuator 72 is a push button 78 housed within a groove 80 formed at the open access end 64. The actuator 72 can be moved between a neutral position and a deployed position. When the actuator 72 is in the neutral position (FIG. 7), the stop member 66 is resiliently biased towards the lock position. As best seen in FIG. 8, when the actuator 72 is in the deployed position (pushed inwardly), the coupling lock mechanism 70 is arranged to move the stop member 66 to retract into the recess 68 in the release position. This can allow the release member 36 to be slid relative to the base member 34 and removed from the base member 34. In certain embodiments, the actuator 72 extends beyond a perimeter 82 of the base member 34 (FIG. 16 and FIG. 18) when in the neutral position. In other embodiments, the actuator 72 does not extend beyond the perimeter 82 of the base member 34 (FIGS. 7 to 9).

Figure 13:
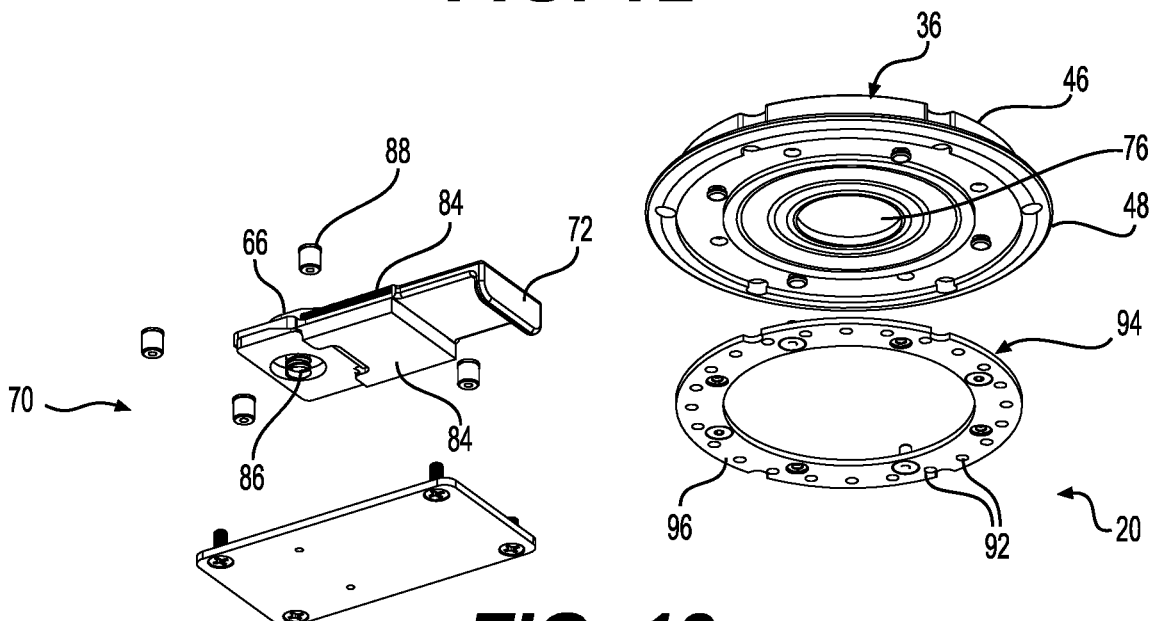
FIG. 13 is an exploded view of the release member of FIG. 7 and a lock mechanism, according to certain other embodiments of the present disclosure.
Figure 14:
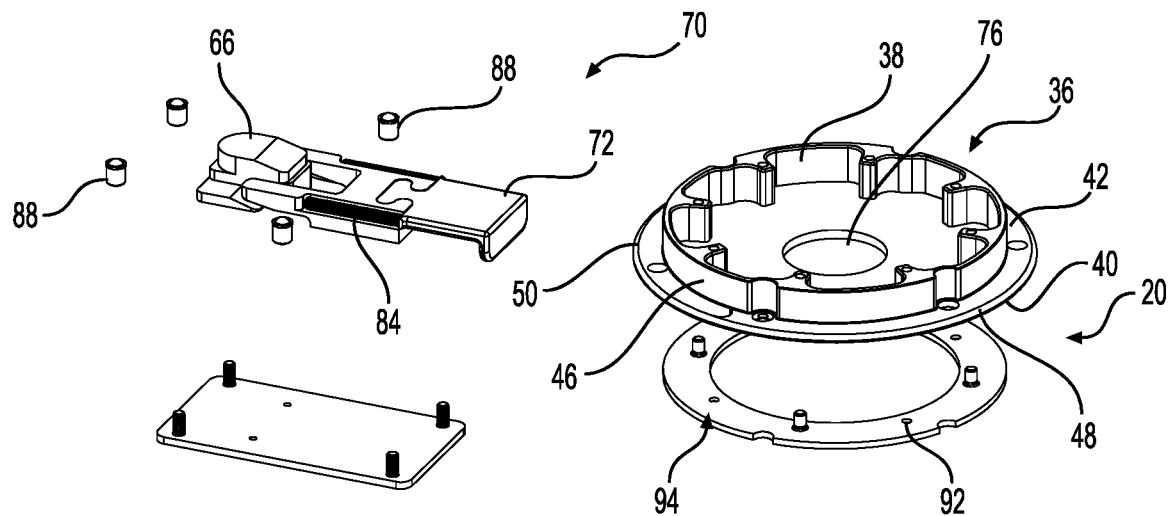
FIG. 14 is an exploded view of the release member of FIG. 7 and a lock mechanism, according to certain other embodiments of the present disclosure.

The coupling lock mechanism 70, best seen in FIGS. 13 and 14, comprises an actuator spring 84 resiliently biasing the actuator 72 outwardly to the neutral position, and a stop member spring 86 resiliently biasing the stop member 66 to the lock position. The actuator spring 84 and the stop member spring 86 extend in directions which are substantially transverse to one another.

The base member 34 comprises a plurality of spring loaded ball bearings 88 partially extending from recesses 90 formed in the planar contact portion 56 of the front side 52 of the base member 34 and engageable with corresponding recesses 92 defined in the planar contact face 44 of the release member 36. The spring loaded ball bearings 88 and the recesses 92 can guide the movement of the release member 36 relative to the base member 34.

Figure 12:
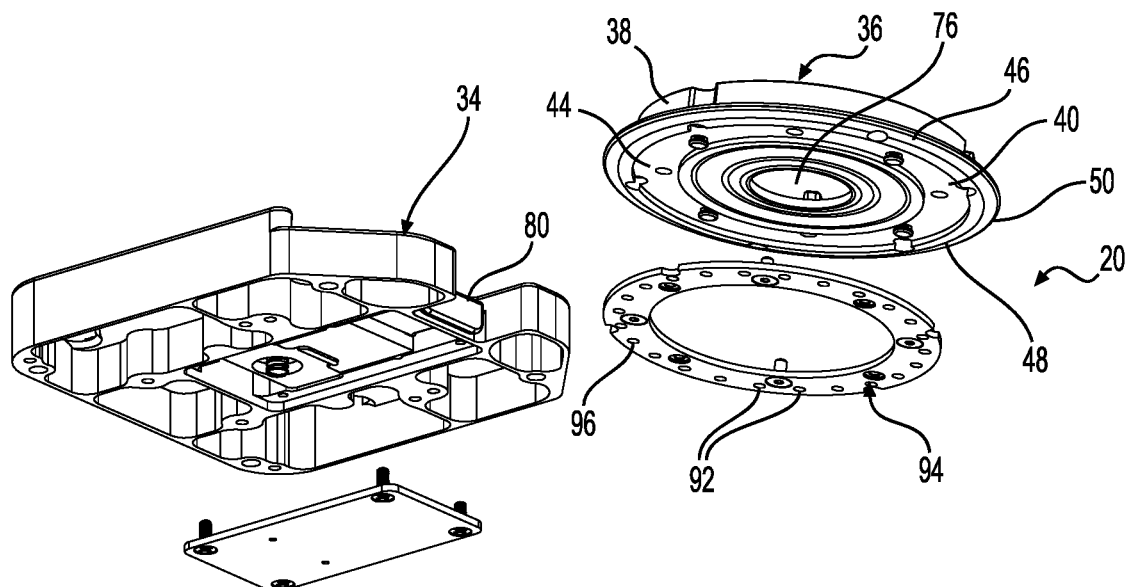
FIG. 12 is an exploded view of the base member and the release member of FIG. 7, according to certain other embodiments of the present disclosure.

In certain embodiments, the planar contact face 44 of the release member 36 comprises an anti-friction layer for reducing or minimizing friction between the contact faces 44, 56 of the release member 36 and the base member 34. As illustrated in FIGS. 12 to 14, the anti-friction layer comprises a disc 94 attached to the release member 36 and with an outer face 96 which is the planar contact face 44 and having anti-friction properties. In this embodiment, the recesses 92 for receiving the spring loaded ball bearings 88 are formed in the disc 94. In other embodiments, the anti-friction layer comprises a coating. The anti-friction layer may comprise any material that reduces friction between the base member 34 and the release member 36.

The coupling device 20 further comprises a top plate 98 attachable to the collar 46 of the release member 36 and attachable to the mobile equipment 12. As best seen in FIG. 7, the top plate 98 is attached to the collar 46 by fasteners 100, such as screws. The top plate has an opening formed therein.

In certain embodiments (for example as illustrated in FIGS. 6 to 14), when the base member 34 and the release member 36 are coupled together and in the lock position, the release member 36 is rotatable within the pocket 62 whilst maintaining the coupling. In this respect, the perimeter 48 of the plate-like body 38 of the release member 36 is circular in shape, the stop member 66 of the base member 34 is positioned substantially centrally of the planar contact portion 56, and the opening 76 of the release member 36 is positioned substantially centrally of the plate-like body 38, such that the release member 36 can be rotated within the pocket 62 when the stop member 66 is in the lock position. The stop member 66 can be considered to function also as a pivot point in these embodiments.

In certain other embodiments (for example as illustrated in FIGS. 16 to 18), when the base member 34 and release member 36 are coupled together and in the lock position, the release member 36 is not rotatable within the pocket 62. In this respect, the perimeter 48 of the plate-like body 38 of the release member 36 has an eccentric shape such that the release member 36 is not rotatable in the pocket 62 of the base member 34. The perimeter 48 of the release member 36 may have a shape which is a multi-faceted geometric form. This embodiment of the coupling device 20 may be used when rotation of the mobile equipment 12 is not required. As illustrated in FIG. 18, in certain embodiments, rotation of the mobile equipment 12 is not required when the mobile equipment 12 is to be mounted to a wall. In the embodiment of FIG. 18, the coupling device 20 is mounted to a master plate 102 which is attachable to rails 104. This configuration is suitable for narrower vehicles, such as ambulance and aircraft. In certain embodiments, the release member 36 further comprises a circular member 106 which is rotatable within the pocket 62 (FIG. 17).

Figure 15:
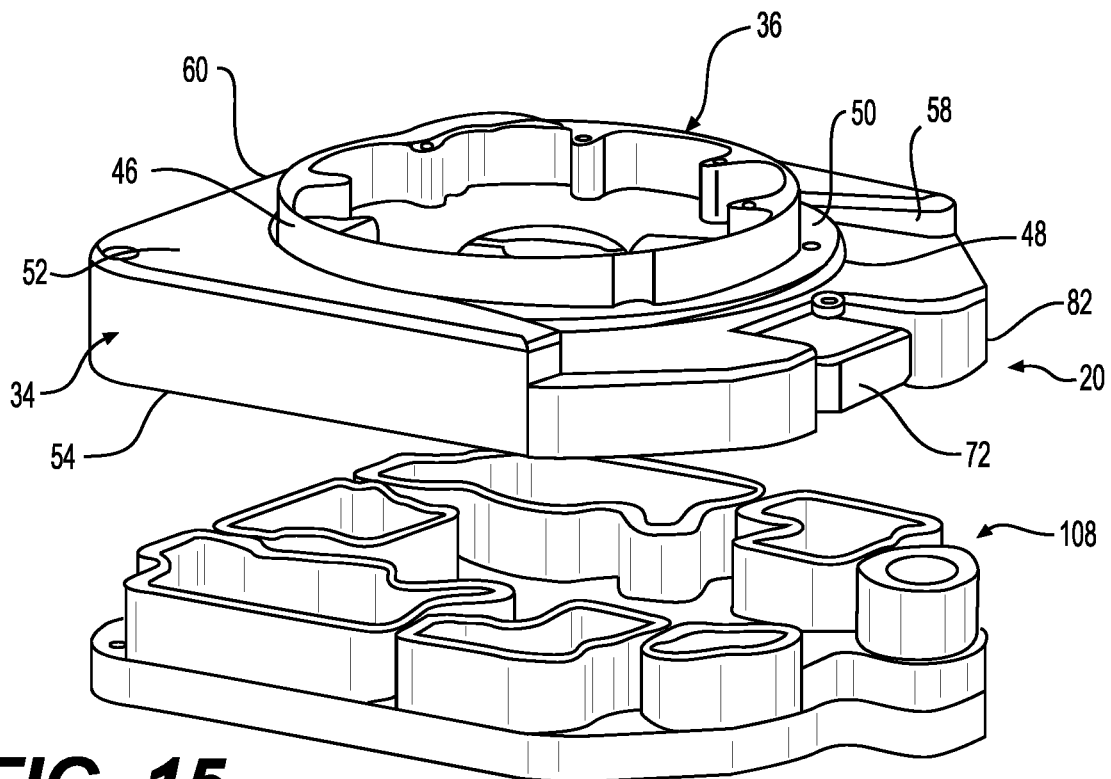
FIG. 15 is the base member of FIG. 7 and a damping member, according to certain other embodiments of the present disclosure.

In certain embodiments, the coupling device 20 is further provided with a damping member 108 (FIG. 15) attachable to the back side 54 of the base member 34 and arranged to be positioned between the base member 34 and the surface in use. The damping member 108 is arranged to absorb vibrations and shocks/reduce energy transmission. In certain embodiments, the damping member 108 is made of any suitable material such as elastomeric materials.

Returning back to the securing apparatus 10 of FIGS. 1 to 6, the base support member 22 of the frame 18 comprises a plate 110 having a top surface 112 for supporting the mobile equipment 12 and raised portions 114 along at least a part of a perimeter 116 of the plate top surface 112. In the embodiments illustrated in FIGS. 1 to 6, the raised portions 114 are blocks spaced from one another on the top surface 112 and along three sides of the perimeter 116 of the base support member 22. The blocks can delimit movement of the mobile equipment 12 in a side to side direction, and a forward direction. It will be appreciated that movement of the mobile equipment 12 in a backwards direction is delimited by the backing support member 26. The plate 110 of the base support member 22 can have any appropriate size and shape for the mobile equipment 12 requiring transportation.

Figure 6:
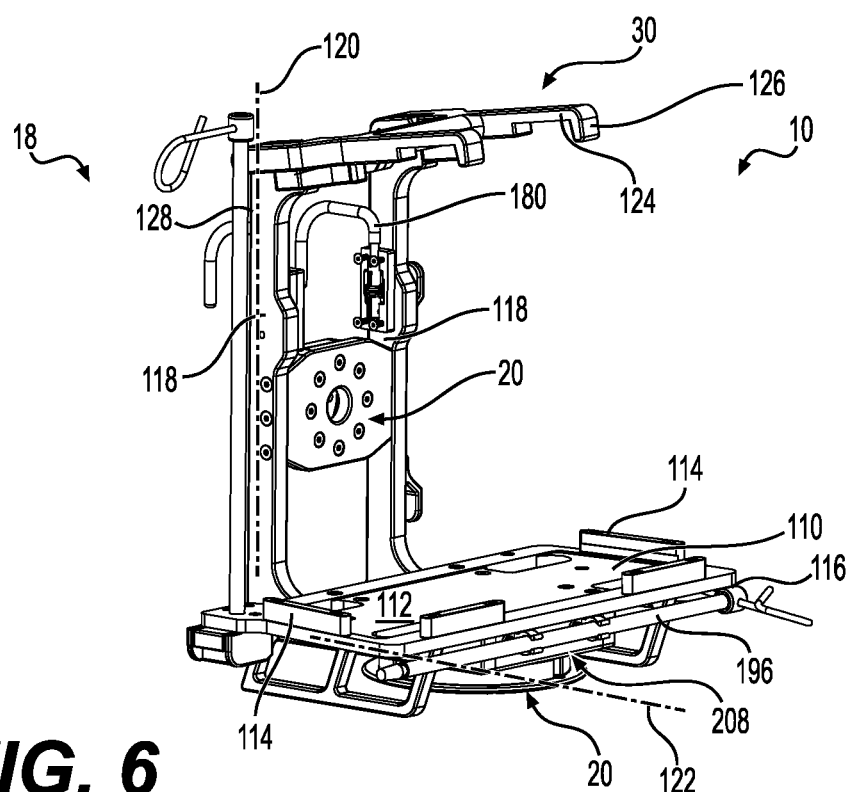
FIG. 6 is a perspective view from the front of a securing apparatus comprising a coupling device, according to certain other embodiments of the present disclosure.

The backing support member 26 comprises a pair of struts 118 extending upwardly from the base support member 22. An axis 120 of the struts 118 is transverse to an axis 122 of the base support member 22 (FIG. 6). The coupling device 20 is positioned between the pair of struts 118 at a distance about midway along the struts 118.

Figure 19:
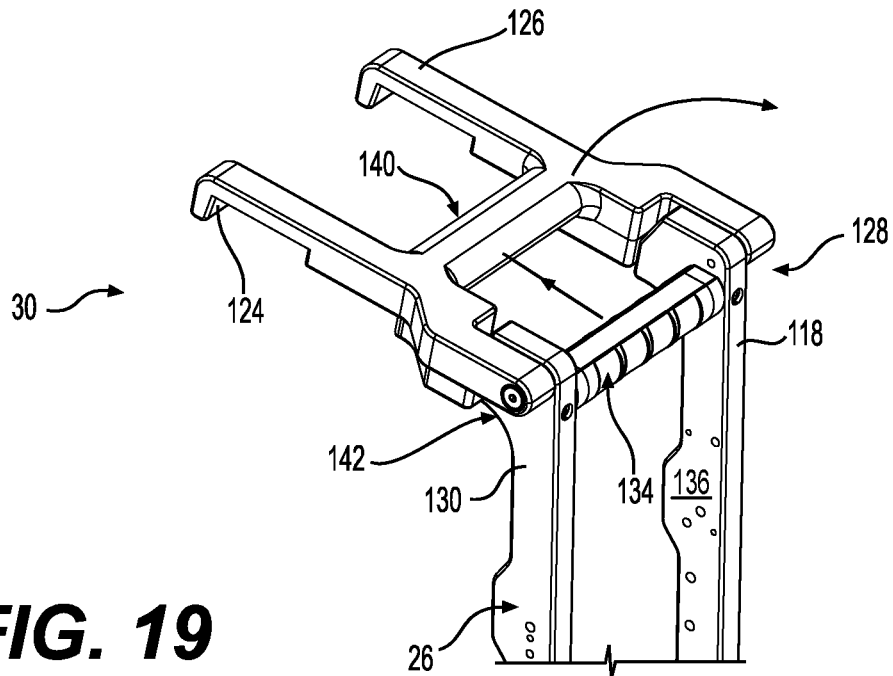
FIG. 19 is a top restraining member of the frame of the securing apparatus of FIG. 1 in a lock position, according to certain embodiments of the present disclosure.
Figure 20:
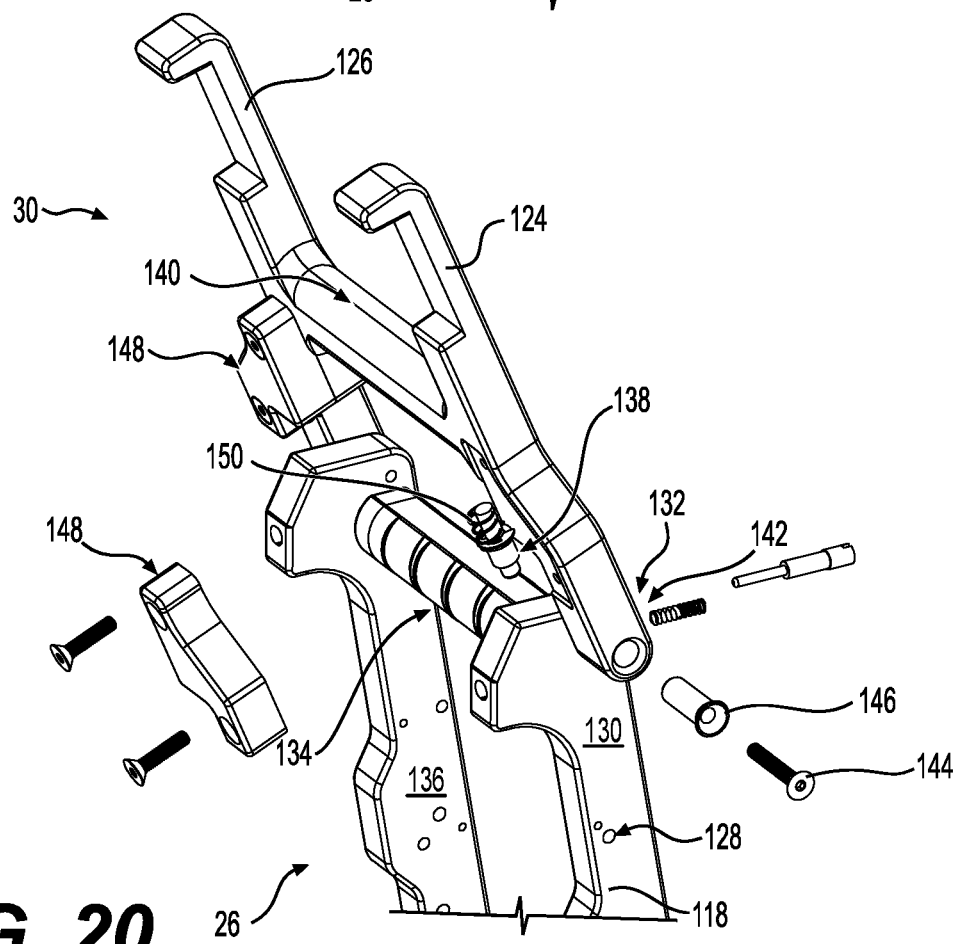
FIG. 20 is the top restraining member of FIG. 19 in an unlock position, according to certain embodiments of the present disclosure.

As best seen in FIGS. 19 and 20, the top restraining member 30 comprises two arms 124, each arm 124 having a proximal end 126 at which it is pivotally attached to a top end 128 of the backing support member 26. The arms 124 are pivotally attached to an outside face 130 of the respective strut 118 of the backing support members 26. Each arm 124 also has a distal end 132 which is claw shaped. A first cross-bar 134 extends between oppositely facing inner faces 136 of the two struts 118, at the proximal ends 126 of the arms 124, and is connected to a locking mechanism 138 for delimiting the movement of the top restraining member 30 relative to the backing support member 26. The first cross-bar 134 is moveable relative to the struts 118 for modulation of the locking mechanism 138 and functions as a moveable handle, in a manner that will be described below.

A second cross-bar 140 extends between the two arms 124 distally from the first cross bar 134. The second cross-bar 140 functions as a fixed handle, in a manner that will be described below.

The top restraining member 30 is arranged to extend across the top face 32 of the mobile equipment 12 in use, and is sized and shaped to accommodate the mobile equipment 12 being transported. The top restraining member 30 is pivotable between a restraining position in which it extends across the top face 32 of the mobile equipment 12, and a release position in which it extends upwardly from the backing support member 26. The locking mechanism 138 is arranged to lock the restraining member 30 in one or both of the restraining position and the release position. With reference to FIGS. 19 and 20, pulling the top restraining member 30, such as by gripping the second cross-bar 140, away from the backing support member 26 causes the release of the locking mechanism 138 and permits modulation from the restraining position to the release position.

The top restraining member 30 is pivotable about a pivot 142 at the top end 128 of the struts 118. Each pivot 142 comprises a screw 144 extending through the respective arm 124 of the top restraining member 30, at the proximal end 126, and extending into a sleeve 146 formed in the respective strut 118 of the backing support member 26. Each sleeve 146 extends in a direction substantially parallel to the first and second cross-bars 134, 140. The sleeve 146 may be made of a self-lubricating material. In certain embodiments, the sleeve is made of a polymeric material such as PTFE.

A housing 148 is attached, such as by screws, to the top end 128 of the struts 118 at the back side and is sized and shaped to abut against an end of the struts 118 to delimit the movement of the top restraining member 30 downwardly.

The second cross-bar 140 is resiliently biased away from the first cross-bar 134, such as by a spring and bolt. Pulling the second cross-bar 140 closer to the first cross-bar 134 pushes against a rod 150 to release a lock and allow rotation of the top restraining member 30. When the top restraining member 30 is rotated downwardly, the spring compresses and allows the lock to retract and re-engage, to block rotation.

Turning now to FIGS. 21-24, in certain embodiments, the securing apparatus 10 comprises at least one clamp 152 for releasably attaching the securing apparatus 10 to the support surface, particularly to rails of the support surface.

The clamp 152 comprises a body 154, a clamping screw 156, a handle 158 and a movable jaw 160. The movable jaw 160 is connected to the clamping screw 156 by means of a fastener. The handle 158 is connected to the clamping screw 156 by a fastener and, in certain embodiments, closed by a cap. A disengagement mechanism 161 of the clamping screw 156 comprises a button 162, a gasket 164 for sealing and a slider 166. These three pieces 162, 164, 166 are connected together by means of a fastener, such as a screw. This assembly is inserted into a base 168 of the body 154 of the clamp 152 and is retained by a fastener. The clamping screw 156 retains a cam 170 which has the same type of thread (in terms of pitch etc) as the clamping screw 156. The cam 170 is assembled with a leaf spring and a screw. To release the clamping screw 156 and speed up the tightening and tightening movements, the disengagement mechanism 161 is caused to engage the cam 170 and cause it to pivot it to disengage the clamping screw 156. Fasteners, such as screws and nuts, serve to secure the clamp 152 to the securing apparatus 10. Engagement of the threads of the cam 170 with the threads of the clamping screw 156 allow the supporting of additional load compared to a conventional clamp.

Figure 21:
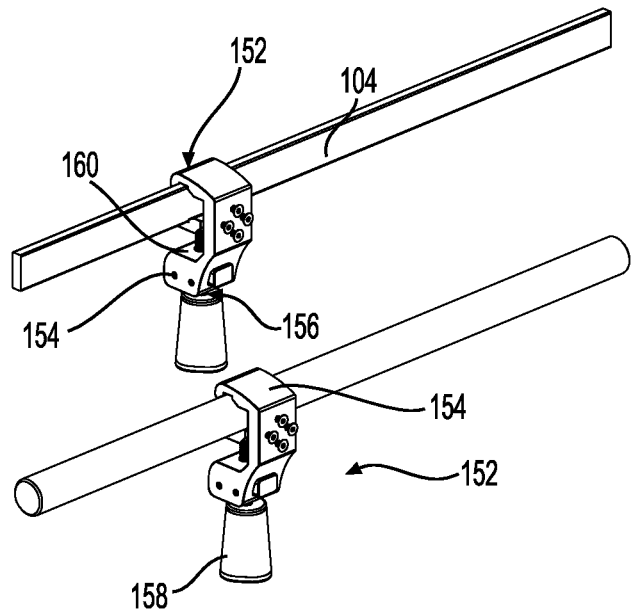
FIG. 21 a clamp for use with the securing apparatus of FIG. 1, according to certain embodiments of the present disclosure.
Figure 22:
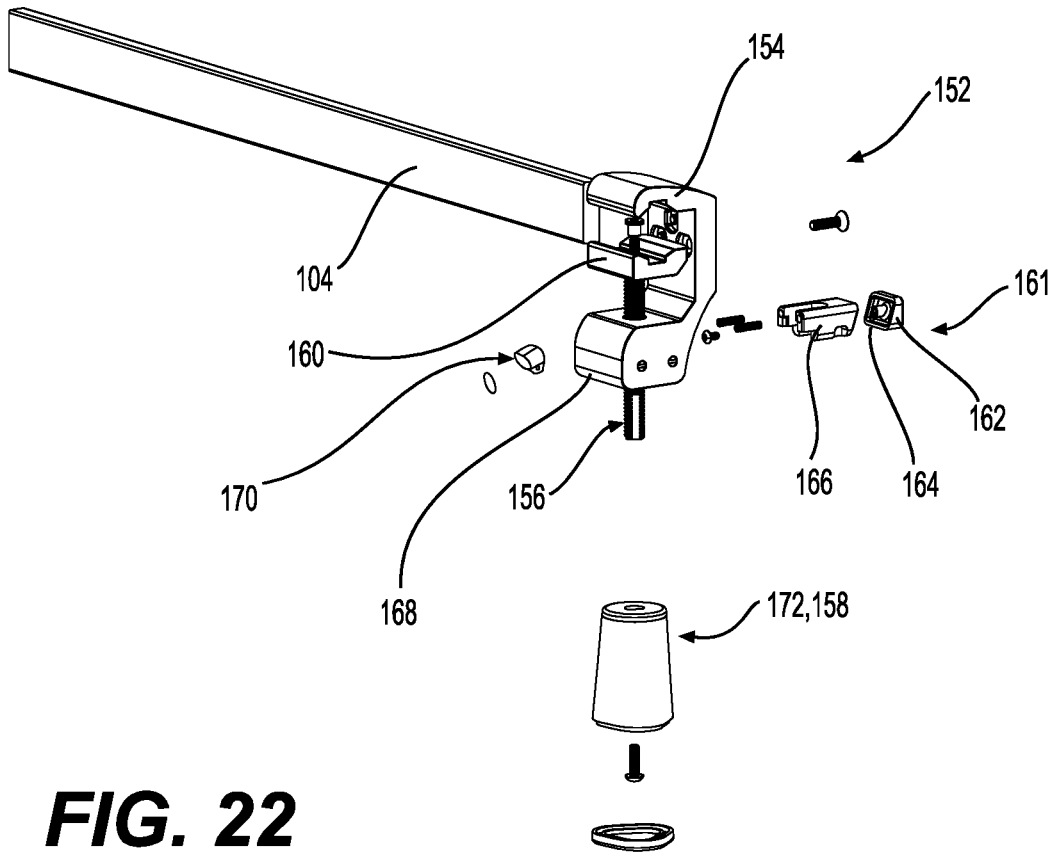
FIG. 22 is an exploded view of the clamp of FIG. 21, according to certain embodiments of the present disclosure.

The clamp 152 of FIGS. 22 and 23 differs from the clamp 152 of FIG. 21 in that it has a clamping handle 172 which has the characteristics of torque wrench so as not to deform the clamp 152 or deform the piece on which the clamp 152 is attached to. The clamping handle 172 comprises a nut 174 which supports the handle 172. A connector 176 is filled and blocked by the nut 174. The connector 176 is round on the outside and has teeth that are square on one side and round on the other. The connector 176 is of the hexagonal type so as to be driven by the handle 172 which has the same internal shape. The connector 176 has a smooth hole in the center to freely rotate around the clamping screw 156. When the handle 172 rotates clockwise in order to tighten a grip of the clamp, the rounded teeth may escape if the pressure exceeds the predetermined value. When the handle 172 rotates counter clockwise to loosen the clamp 152, the square teeth remain hooked and allow loosening. A spring is provided which is in compression between the piece and a washer. A washer, a self-locking nut and a cap are also provided.

Figure 25:
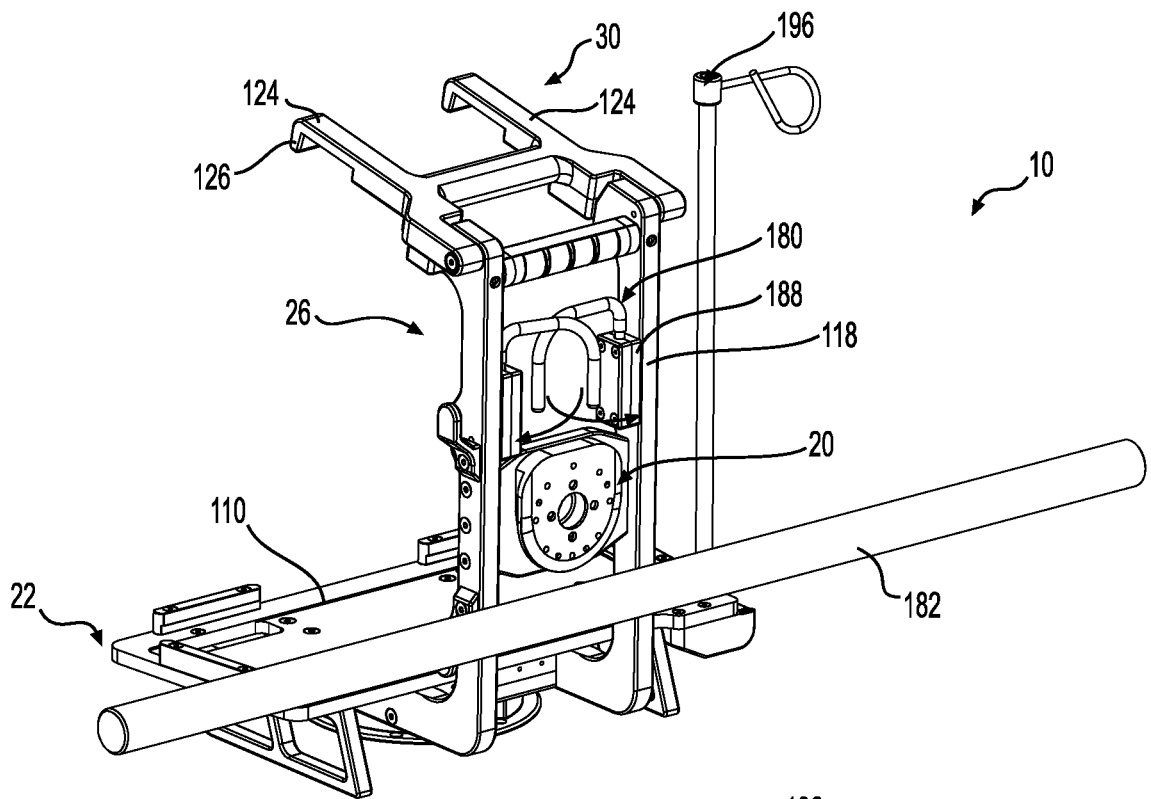
FIG. 25 is a securing apparatus including hooks in a folded position, according to certain other embodiments of the present disclosure.
Figure 26:
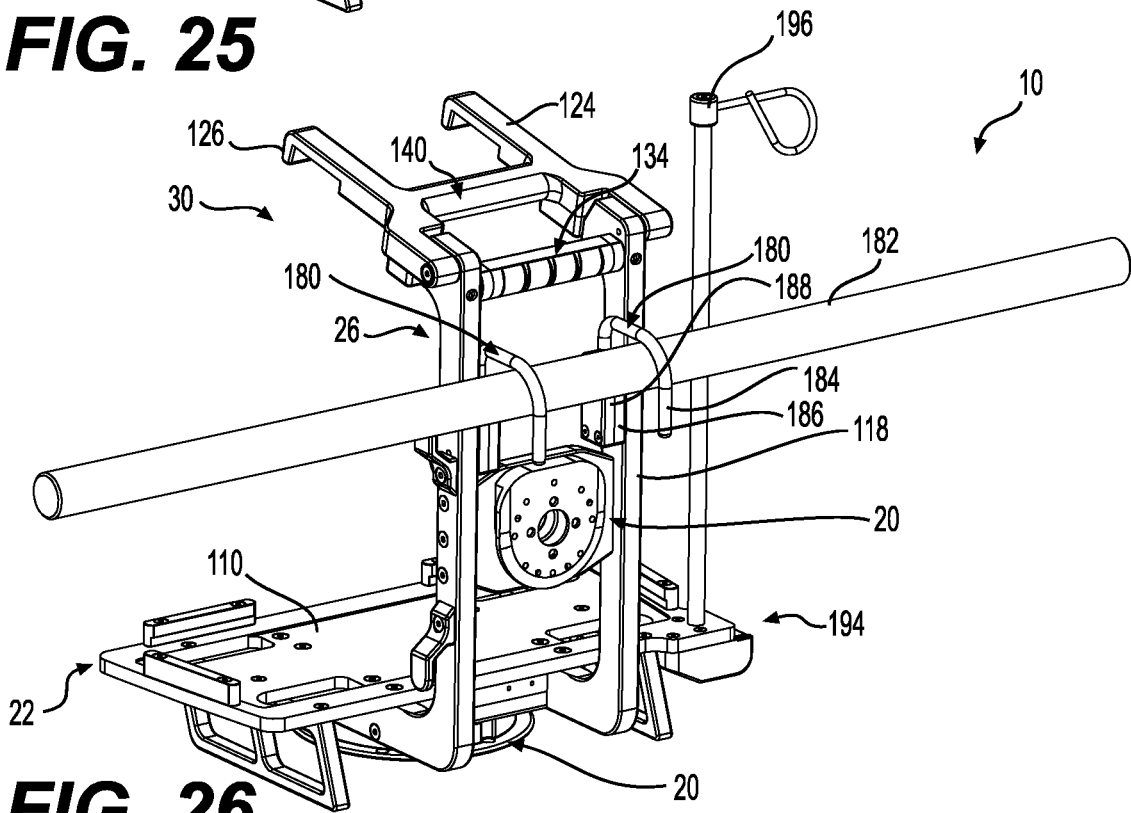
FIG. 26 is the securing apparatus of FIG. 25 with the hooks in a deployed position, according to certain other embodiments of the present disclosure.
Figure 27:
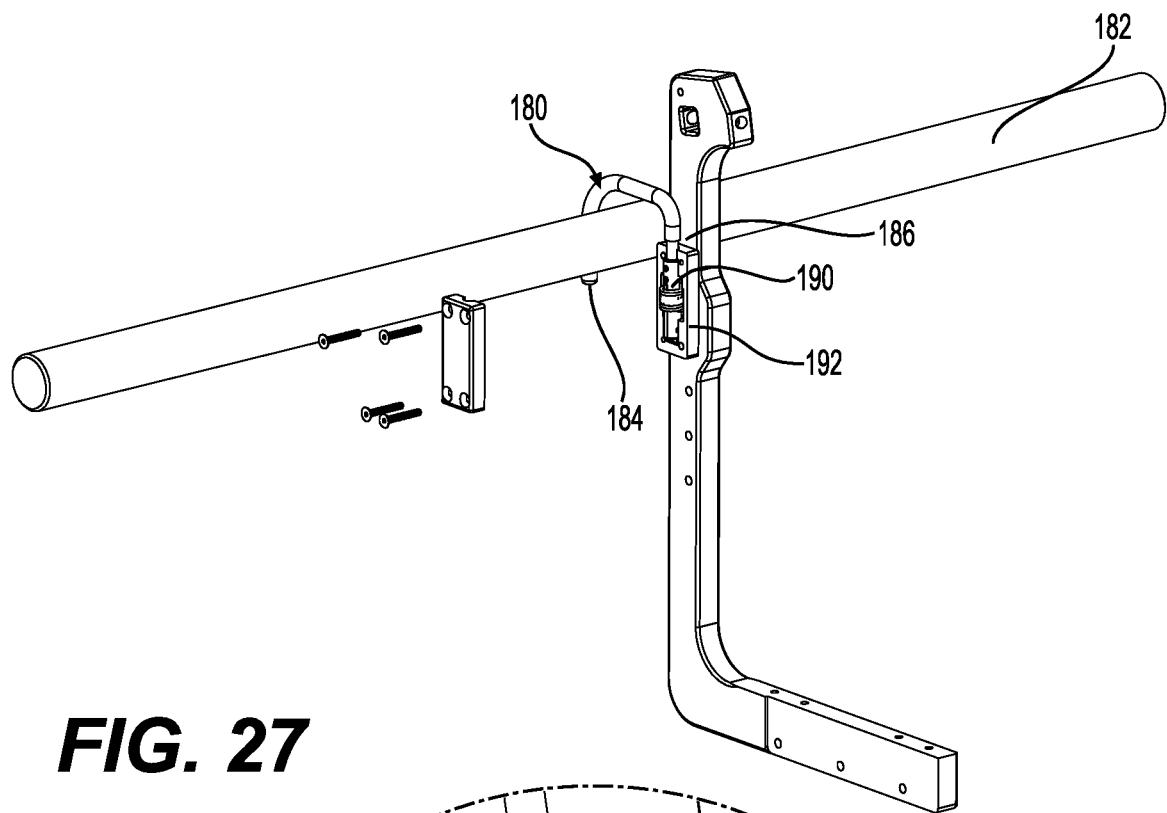
FIG. 27 is a close up of the hook of FIG. 25 and FIG. 26 and showing a hook lock mechanism in an exploded view, according to certain other embodiments of the present disclosure.

In certain embodiments (FIGS. 25-28), the securing apparatus 10 comprises two hooks 180 attached to the frame 18 for releasably attaching the securing apparatus 10 to a horizontal support member 182, such as a pole or rail, on the support surface. As best seen in FIGS. 25 to 27, each hook 180 has a free end 184 and a pivot end 186. Each hook 180 is pivotably attached to the struts 118 of the backing support member 26 by the pivot end 186. Each hook 180 is moveable between a deployed position in which the free end 184 extends away from the support member 182, and a retracted position in which the two hooks 180 lie substantially flat. The hooks 180 are resiliently biased to the storage position by a swivel hook mechanism 188 (FIG. 27) in which they are arranged to overlap one another. The swivel hook mechanism 188 comprises spring pins 190 attached to the pivot end 186 of the hook 180, and contained in a housing 192.

Figure 28:
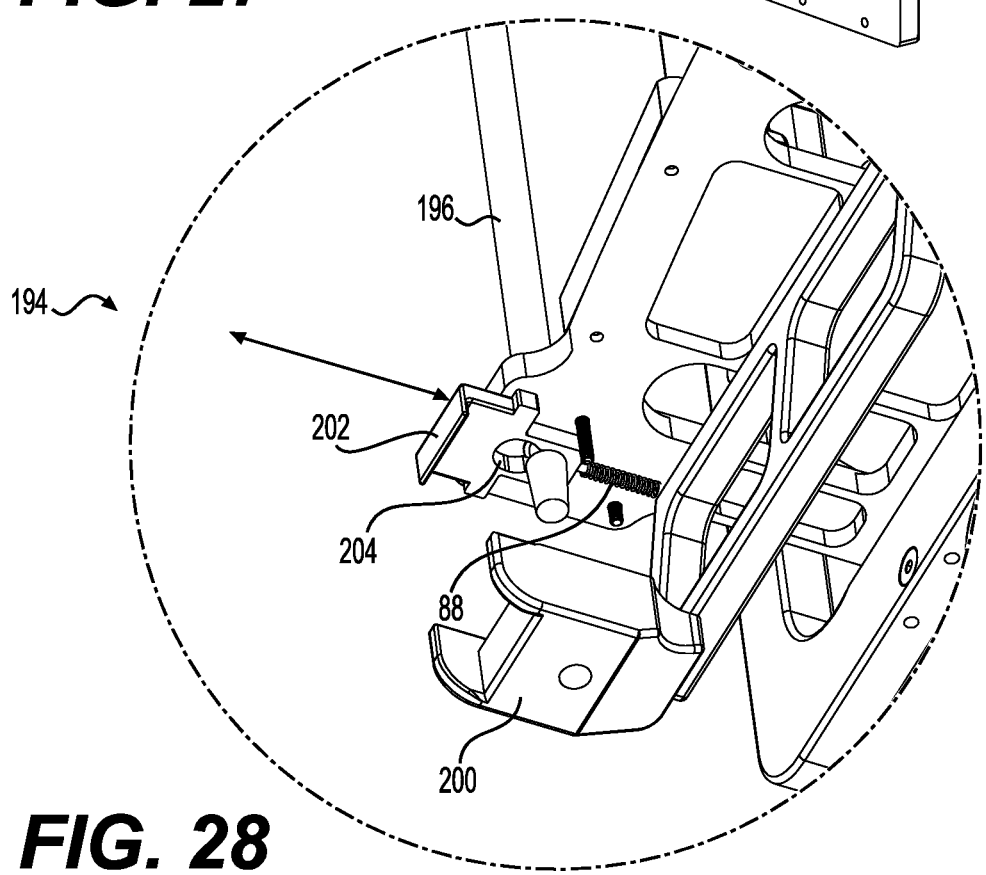
FIG. 28 is a close-up of an IV pole mounting member and an IV pole locking mechanism, according to certain other embodiments of the present disclosure.

In certain embodiments, the securing apparatus 10 comprises an IV pole mounting member 194, for mounting an IV pole 196 in a substantially vertical position, ready for use. There is also provided, in certain embodiments, an IV pole locking mechanism 198 (FIG. 28) for securing the IV pole 196 in the IV pole mounting member 194. FIG. 28 is a close-up of the IV pole locking mechanism 198. The IV pole locking mechanism 198 comprises a housing 200 including a locking plate 202 having a rod lock slot 204, through which an end of the IV pole 196 is extended, and a spring 206 resiliently biasing the plate 202 away from the securing apparatus 10. Exerting a force on the locking plate 202 engages an edge of the rod lock slot 204 into a notch in the end of the IV pole 196 to retain the IV pole 196 in position.

In certain embodiments, the securing apparatus 10 comprises an IV pole storage member 208 attached to the base support member 22 of the frame 18 and which is arranged to receive and secure an IV pole 109 in a horizontal storage position whilst not in use (FIG. 6). The IV pole storage member 208 can be a clip or other fastener for securing the IV pole.

Figure 29:
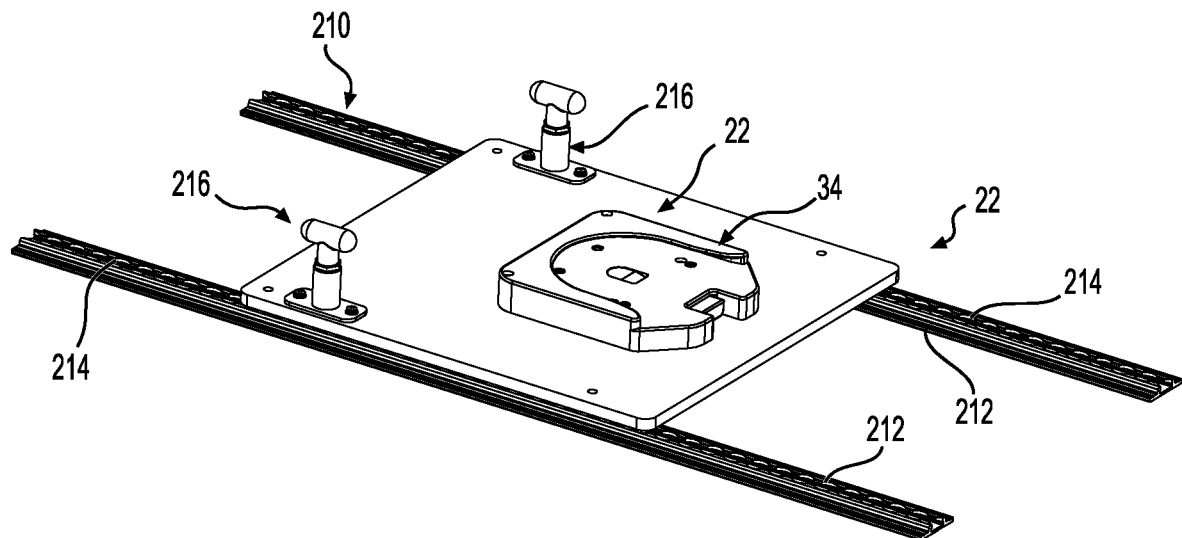
FIG. 29 is a base member of the coupling device of FIG. 7 attached to a based support member and an attachment system for attaching to a rail, according to certain other embodiments of the present disclosure.
Figure 30:
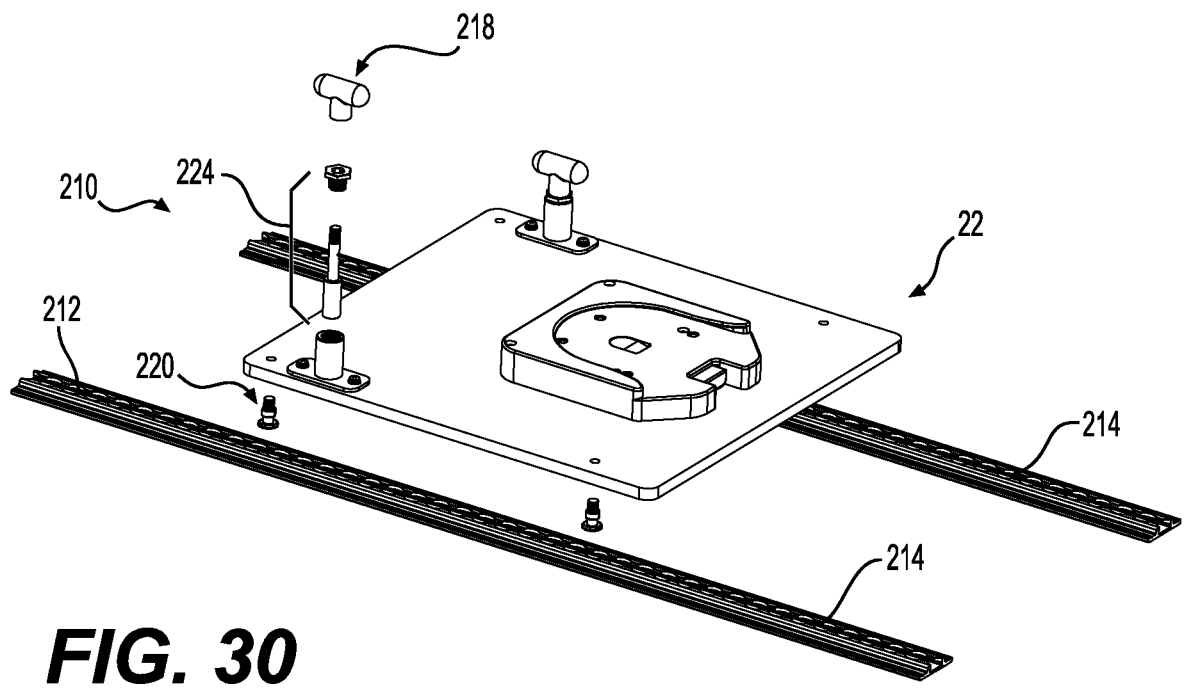
FIG. 30 is the base member of FIG. 29 and showing the attachment system as an exploded view.

In certain embodiments, the securing apparatus 10 is arranged to secure the mobile equipment 12 to a floor rail system 210 (FIGS. 29 and 30). The floor rail system 210 may be part of a rail transportation system along which the securing apparatus 10 can be moved. The floor rail system 210 may be attached to a floor of an aircraft, for example. In the floor rail system 210, there is provided a pair of rails 212 may be provided as a track. Each rail 212 has a series of openings 214 formed therein and extending along the rail 212.

Figure 10:
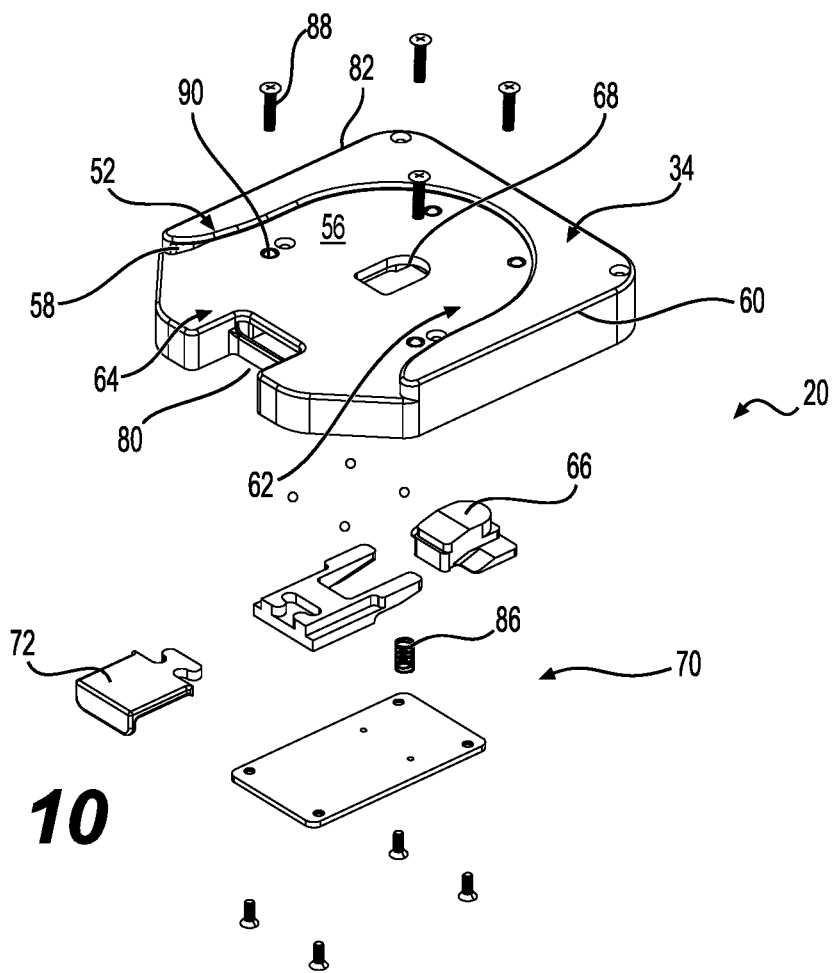
FIG. 10 is an exploded view of the base member of FIG. 7, according to certain other embodiments of the present disclosure.
Figure 11:
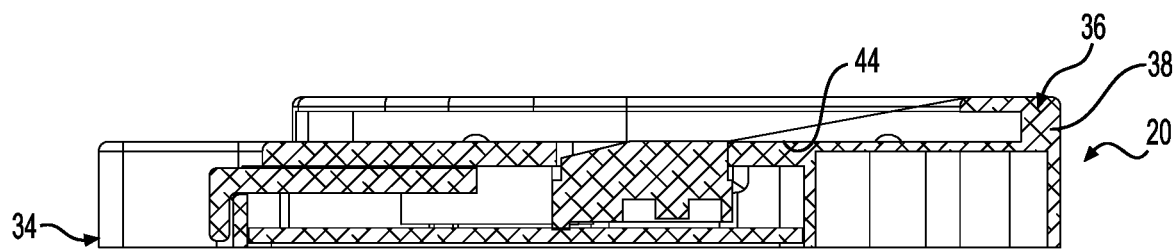
FIG. 11 is a cross-sectional view of the coupling device of FIG. 8, according to certain other embodiments of the present disclosure.

The frame 18 of the securing apparatus 10 comprises a base support member 22 to which is attached the coupling device 20 of FIGS. 9 and 10 (non-rotatable). An attachment system 216 is provided for attaching the base support member 22 to the rail 212. The attachment system 216 comprises a handle component 218 for locking and releasing the base support member 22 to the rail 212 via pins 220 which can engage in the openings 214 in the rail 212. A spring-loaded latch mechanism 224 is used to retain the pins 220 in the openings 214 to lock the position of the securing apparatus 10 on the rails 212.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein.

It should be appreciated that the invention is not limited to the particular embodiments described and illustrated herein but includes all modifications and variations falling within the scope of the invention as defined in the appended claims.

The invention claimed is:

1. A coupling device for releasably securing a first item to a second item, the coupling device comprising a base member connectable to the first item, and a release member connectable to the second item, the base member and the release member being releasably connectable together in a lockable coupled position;
the base member having a front face including a contact portion for contacting a contact face of the release member in the coupled position;
the release member comprising a body, at least a portion of the body being configured to be received in a pocket on the front face of the base member when the base member and the release member are in the coupled position, the pocket having an open access end through which the release member can be slidingly inserted and removed;
a stop member positioned substantially centrally of the contact portion, the stop member moveable, by an actuator, between a lock position in which the stop member interengages with the release member to prevent removal of the release member from the pocket of the base member, and a release position in which the release member can be separated from the base member.

2. The coupling device of claim 1, wherein the open access end is at a same end of the base member as the actuator.

3. The coupling device of claim 1, wherein the stop member is positioned in a recess within the contact portion and moveable by the actuator which is connected to a resilient lock mechanism between the lock position in which at least a portion of the stop member extends from the recess and abuts an edge of an opening defined in the release member contact face in the coupled position, and a release position in which the stop member is retracted into the recess.

4. The coupling device of claim 1, wherein at least a portion of the stop member comprises a wedge, a thinner end of the wedge facing the open access end of the pocket, and wherein the resilient lock mechanism is configured to permit the stop member to move into the recess as the release member is slid into the pocket.

5. The coupling device of claim 1, wherein the actuator has a neutral position and a deployed position, wherein when the actuator is in the neutral position, the stop member is resiliently biased towards the lock position.

6. The coupling device of claim 1, wherein the base member comprises a plurality of spring loaded ball bearings partially extending from recesses formed in the front face of the base member and engageable with corresponding recesses defined in the contact face of the release member.

7. The coupling device of claim 1, wherein the contact face of the release member has an anti-friction layer.

8. The coupling device of claim 1, further comprising a damping member attachable to a back face of the base member and arranged to be positioned between the base member and the first item in use, the damping member being arranged to absorb vibration and/or shock.

9. The coupling device of claim 1, further comprising a top plate attachable to the collar of the release member and attachable to the second item.

10. The coupling device of claim 1, wherein the base member has a shoulder extending around a portion of a periphery of the contact portion to define the pocket for receiving the release member, the open access end being at a portion of the periphery without the shoulder.

11. The coupling device of claim 10, wherein the release member has a flange and the shoulder is engageable with a portion of the flange when the release member is positioned on the base member.

12. The coupling device of claim 10, wherein the shoulder is configured to delimit movement of the release member orthogonally away from the front face of the base member, when the base member and the release member are in the coupled position.

13. The coupling device of claim 1, wherein the body of the release member has an opening for receiving the stop member in the lock position, the opening having an edge, and at least a portion of the edge of the opening and at least a portion of the stop member are configured to interengage in the lock position.

14. The coupling device of claim 13, wherein the opening defined in the body of the release member is circular.

15. The coupling device of claim 13, wherein the stop member and the opening are relatively sized and shaped so that the release member can be rotated within the pocket, with the stop member as a rotation point when the release member is coupled to the base member.

16. The coupling device of claim 15, wherein there are provided a plurality of spring loaded ball bearings partially extending from recesses formed in one of: the front face of the base member or the contact face of the release member, which are engageable with corresponding recesses defined in the other of the front face of the base member or the contact face of the release member.

17. A coupling device for releasably securing a mobile equipment to a support surface, the coupling device comprising a base member connectable to the support surface, and a release member connectable to the mobile equipment, the base member and the release member being releasably connectable together in a coupled position;

the release member comprising a plate-like body with a first side, the first side defining a planar contact face, and a second side having a collar extending therefrom, the collar positioned inwardly of a perimeter of the release member to define a flange portion;

the base member having:
a front face including a planar contact portion for contacting the contact face of the release member;
a shoulder extending around a portion of a periphery of the planar portion to define a pocket for receiving the release member, the shoulder engageable with a portion of the flange of the release member when the release member is positioned on the base member;
an open access end through which the release member can be slidingly inserted and removed from the pocket;
a stop member positioned in a recess defined substantially centrally of the planar contact portion, the stop member moveable by a resilient lock mechanism and an actuator between a lock position in which at least a portion of the stop member extends from the recess and abuts an edge of an opening defined in the release member contact face in the coupled position, and a release position in which the stop member is retracted into the recess;
the actuator having a neutral position and a deployed position, wherein when the actuator is in the neutral position, the stop member is resiliently biased towards the lock position.

18. The coupling device of claim 17, wherein the base member comprises a plurality of spring loaded ball bearings partially extending from recesses formed in the front face of the base member and engageable with corresponding recesses defined in the planar contact face of the release member.

19. The coupling device of claim 17, wherein there are provided a plurality of spring loaded ball bearings partially extending from recesses formed in one of: the front face of the base member or the contact face of the release member, which are engageable with corresponding recesses defined in the other of the front face of the base member or the contact face of the release member.

20. The coupling device of claim 17, wherein the perimeter of the plate-like body of the release member is circular in shape, and the opening of the release member is positioned substantially centrally of the plate-like body, such that the release member can be rotated within the pocket when the stop member is in the lock position.

21. A coupling device comprising a base member releasably connectable to a release member in a lockable coupled position, the base member comprising:
a front face having a shoulder extending around a portion of the front face to define a pocket with an open access end for receiving the release member through the open access end, the shoulder being configured to delimit movement of the release member orthogonally to the front face;
a stop member moveable, by an actuator on the base member, between a lock position and a release position, wherein, in use when the release member is received in the pocket, in the lock position the stop member can engage with the release member to prevent removal of the release member through the open access end, and in the release position the release member can slide out of the open access end, and wherein the release member is configured to rotate relative to the base member in the coupled position with the stop member as a rotation point.

22. The coupling device of claim 21, wherein a perimeter of the release member is circular and the opening in the release member is circular.

23. The coupling device of claim 21, wherein there are provided a plurality of spring loaded ball bearings partially extending from recesses formed in one of: the front face of the base member or a contact face of the release member, which are engageable with corresponding recesses defined in the other of the front face of the base member or the contact face of the release member.

\* \* \* \* \*